(12) United States Patent
Pease et al.

(10) Patent No.: US 6,667,394 B2
(45) Date of Patent: *Dec. 23, 2003

(54) PRINTING OLIGONUCLEOTIDE ARRAYS

(75) Inventors: R. Fabian Pease, Stanford, CA (US); Glenn McGall, Mountain View, CA (US); Martin J. Goldberg, San Jose, CA (US); Richard P. Rava, Palo Alto, CA (US); Stephen P. A. Fodor, Palo Alto, CA (US); Virginia Goss, Santa Barbara, CA (US); Lubert Stryer, Stanford, CA (US); James L. Winkler, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/841,405

(22) Filed: Apr. 24, 2001

(65) Prior Publication Data

US 2002/0147319 A1 Oct. 10, 2002

Related U.S. Application Data

(63) Continuation of application No. 09/427,850, filed on Oct. 26, 1999, now Pat. No. 6,239,273, which is a continuation of application No. 09/093,843, filed on May 22, 1998, now abandoned, which is a continuation of application No. 08/635,272, filed on Apr. 19, 1996, now Pat. No. 5,831,070, which is a continuation of application No. 08/395,604, filed on Feb. 27, 1995, now Pat. No. 5,599,695.

(51) Int. Cl.[7] ............. C07H 21/00; C07H 21/02; C07K 1/00
(52) U.S. Cl. .............. 536/25.3; 536/22.1; 536/23.1; 530/350; 530/387.1
(58) Field of Search ............. 536/23.3, 23.1, 536/22.1; 530/350, 387.1

(56) References Cited

U.S. PATENT DOCUMENTS

| | | | |
|---|---|---|---|
| 4,016,855 A | 4/1977 | Mimata | 125/13 |
| 4,401,796 A | 8/1983 | Itakura | 525/340 |
| 4,458,066 A | 7/1984 | Caruthers et al. | 536/27 |
| 4,500,707 A | 2/1985 | Caruthers et al. | 536/27 |
| 4,507,433 A | 3/1985 | Miller et al. | 536/24.5 |
| 5,094,594 A | 3/1992 | Brennan | 417/413.2 |
| 5,143,854 A | 9/1992 | Pirrung et al. | 436/518 |
| 5,200,051 A | 4/1993 | Cozzette et al. | 204/403.7 |
| 5,242,974 A | 9/1993 | Holmes | 525/54.11 |
| 5,318,679 A | 6/1994 | Nishioka | 204/157.68 |
| 5,384,261 A | 1/1995 | Winkler et al. | 436/518 |
| 5,424,186 A | 6/1995 | Fodor et al. | 435/6 |
| 5,449,754 A | 9/1995 | Nishioka | 530/334 |
| 5,472,672 A | 12/1995 | Brennan | 422/131 |
| 5,474,796 A | 12/1995 | Brennan | 427/2.13 |
| 5,489,678 A | 2/1996 | Fodor et al. | 536/25.4 |
| 5,514,789 A | 5/1996 | Kempe | 536/25.4 |
| 5,527,681 A | 6/1996 | Holmes | 435/6 |
| 5,545,531 A | 8/1996 | Rava et al. | 435/6 |
| 5,556,752 A | 9/1996 | Lockhart et al. | |
| 5,599,695 A * | 2/1997 | Pease et al. | 435/91.1 |
| 5,700,637 A | 12/1997 | Southern | 435/6 |
| 5,738,829 A * | 4/1998 | Kempe et al. | 422/107 |
| 5,831,070 A * | 11/1998 | Pease et al. | 536/25.3 |
| 6,239,273 B1 * | 5/2001 | Pease et al. | 536/25.3 |

FOREIGN PATENT DOCUMENTS

| | | |
|---|---|---|
| EP | 0 045 665 B1 | 2/1982 |
| EP | 0 373 203 B1 | 11/1989 |
| EP | 0 619 321 | 6/1990 |
| GB | 2 182 336 | 5/1987 |
| WO | WO 89/10977 | 11/1989 |
| WO | WO 90/05746 | 5/1990 |
| WO | WO 90/05749 | 5/1990 |
| WO | WO 90/05785 | 5/1990 |
| WO | WO 90/15070 | 12/1990 |
| WO | WO 92/10092 | 6/1992 |
| WO | WO 93/09668 | 5/1993 |
| WO | WO 94/10128 | 5/1994 |
| WO | WO 94/27719 | 12/1994 |
| WO | WO 94/00530 | 1/1995 |
| WO | WO 95/25116 | 9/1995 |
| WO | WO 95/33846 | 12/1995 |

OTHER PUBLICATIONS

Maskos et al, "A novel method for the analyssi of multiple sequence variants by hybridization to oligonucleotides", Nucleic Acids Research 21(9):2267–2268 (1993).*

Almquist et al., "Synthesis and biological activity of a ketomethylene analogue of a tripeptide inhibitor of angiotensin converting enzyme," *J. med. Chem.*, 23:1392–1398 (1980).

Atkinson et al., "Solid phase synthesis of oligodeoxyribonucleotides by the phosphitetriester method," Chapter 3 in *Oligonucleotide Synthesis: A practical approach.* Gait ed., IRL Press: Oxford, New York, pp.35–81 (1984).

Barnett et al., "Debenzoylation of N–benzoylnucleoside derivatives with ethylenediamine–phenol," *Tetrahedron Lett.*, 22:991–994 (1981).

Beaucage et al., "Deoxynucleoside phosphoramidites–A new class of key intermediates for deoxypolynucleotide synthesis," *Tetrahedron Lett.*, 22(20):1859–1862 (1981).

Boal et al., "Cleavage of oligodeoxyribonucleotides from controlled–pore glass supports and their rapid deprotection by gaseous amines," *Nucl. Acids Res.*, 24(15):3115–3117 (1996).

(List continued on next page.)

*Primary Examiner*—Jeffrey Fredman
(74) *Attorney, Agent, or Firm*—Banner & Witcoff, Ltd.

(57) ABSTRACT

A method and apparatus for selectively applying a print material onto a substrate for the synthesis of an array of oligonucleotides at selected regions of a substrate. The print material includes a barrier material, a monomer sequence, a nucleoside, a deprotection agent, a carrier material, among other materials. The method and apparatus also relies upon standard DMT based chemistry, and a vapor phase deprotection agent such as solid TCA and the like.

39 Claims, 16 Drawing Sheets

OTHER PUBLICATIONS

Bos et al., "Amino–acid substitutions at codon 13 of the N–ras oncogene in human acute myeloid leukaemia," *Nature*, 315:726–730 (1985).

Bray et al., "Simultaneous multiple synthesis of peptide amides by the multipin method: Application of vapor–phase ammonolysis," *J. Org. Chem.*, 59:2197–2203 (1994).

Caruthers et al., "New methods for synthesizing deoxyoligonucleotides," *Genetic Engineering*, 4:1–17 (1982).

Chaiken, "Semisynthetic peptides and proteins," *CRC Crit. Rev. Biochem.*, 11:255–301 (1981).

Elder, "Analysis of DNA oligonucleotic hybridization data by maximum entropy," *Maximum Entropy and Bayesian Methods*, Proc. $12^{th}$ International. Workshop, Paris, France, pp. 363–371 (1993).

Evans et al., "Design of non–peptidal ligands for a peptide receptor: cholecystokinin antagonists," *J. Med. Chem.*, 30:1229–1239 (1987).

Fauchére, "Elements for the rational design of peptide drugs," *Adv. Drug Res.*, 15:29–69 (1986).

Feldman et al., "Gray code masks for sequencing by hybridization," *Genomics*, 23:233–235 (1994).

Froehler et al., "Nucleoside H–phosphonates: Valuable intermediates in the synthesis of deoxyoligonucleotides," *Tetrahedron Lett.*, 27(4):469–472 (1986).

Froehler et al., "Synthesis of DNA via deoxynucleotides H–phosphonate intermediates," *Nucl. Acids Res.*, 14(13):5399–5407 (1986).

Goldberg et al., "Screen printing: A technology for the batch fabrication of integrated chemical–sensor arrays," *Sensors & Actuators*, 21(3):171–183 (1994).

Guo et al., "Direct flourescence analysis of genetic polymorphisms by hybridization with oligonculeotide arrays on glass supports," *Nucl. Acids Res.*, 22(24):5456–5465 (1994).

Gutte, "The total synthesis of an enzyme with ribonuclease A activity," *J. Am. Chem. Soc.*, 91(2):501–502 (1969).

Hann et al., "On the double bond isostere of the peptide bond: Preparation of an enkephalin analogue," *J.C.S. Perkin*, 1:307–314 (1982).

Hochgeschwender et al., "Preferential expression of a defined T–cell receptor β–chain gene in hapten–specific cytotoxic T–cell clones," *Nature*, 322:376–378 (1986).

Hogrefe et al., "Deprotection of methylphosphonate oligonucleotides using a novel one–pot procedure," *Nucl. Acids Res.*, 21(9):2031–2038 (1993).

Holladay et al., "Synthesis of hydroxyethylene and ketomethylene dipeptide isoteres," *Tetrahedron Lett.*, 24(41):4401–4404 (1983).

Hruby, "Conformational restrictions of biologically active peptides via amino acid side chain groups," *Life Sciences*, 31:189–199 (1982).

Hudson et al., "Methionine enkephalin and isosteric analogues," *Int. J. Peptide Protein Res.*, 14:177–185 (1979).

Jennings–White et al., "Synthesis of ketomethylene analogs of dipeptides," *Tetrahedron Lett.*, 23(25):2533–2534 (1982).

Jones, "Preparation of protected deoxyribonucleosides," Chapter 2 in *Oligonucleotide Synthesis: A Practical Approach*. Gait ed., IRL Press: Oxford, New York, pp.23–34 (1984).

Kaiser et al., "Peptide and protein synthesis by segment synthesis–condensation," *Science*, 243:187–192 (1989).

Kent, "Chemical synthesis of peptides and proteins," *Ann. Rev. Biochem.*, 57:957–989 (1988).

Maskos et al., A novel method for the analysis of multiple sequence variants by hybridization to oligonucleotides,: *Nucl. Acids Res.*, 21(9):2267–2268 (1993).

Matteucci et al., "Synthesis of deoxyoligonucleotides on a polymer support," *J. Am. Chem. Soc.*, 103(11):3185–3191 (1981).

McGillis, "Lithography," Chapter 7 in *VLSI Technology*, S.M. Sze, ed., McGraw Hill: New York, pp. 267–301 (1983)

Merrifield, "Solid phase synthesis," *Science*, 232:341–347 (1986).

Mikami et al., "A new patterning process concept for large–area transistor circuit fabrication without using an optical mask aligner," *IEEE Trans. Electron Devices*, 41(3):306–314 (1994).

Morley, "Modulation of the action of regulatory peptides by structural modification," *Trends Pharm. Sci.*, 1:463–468 (1980).

Pease et al., "Light–generated oligonucleotide arrays for rapid DNA sequence analysis," *PNAS USA*, 91:5022–5026 (1994).

Pease, "Printing Oligonucleotide Arrays," Affeymetrix Corporation, 14 pages (Sep. 8, 1994).

Polushin et al., "Rapid deprotection procedures for synthetic oligonucleotides," *Nucl. Acids Symp. Ser.*, 24:49–50 (1991).

Reichmanis et al., "O–nitrobenzyl photochemistry: Solution vs. solid–state behavior," *J. Polymer Sci.: Polymer Chem. Ed.*, 23:1–8 (1985).

Rizo et al., "Constrained peptides: Models of bioactive peptides and protein substructures," *Annu. Rev. Biochem.*, 61–387–418 (1992).

Sinha et al., "β–cyanoethyl–N,N–dialkylamino/N–morpholinomonochloro phosphoramidites, new phosphylating agents facilitating ease of deprotection and work–up of synthesized oligonucleotides," *Tetrahedron Lett.*, 24(52):5843–5846 (1983).

Sinha et al., "Polymer support oligonucleotide synthesis XVIII: Use of β–cyanoethyl–N,N–dialkylamino–/N–morpholino phosphoramidite of deoxynucleosides for the synthesis of DNA fragments simplifying deprotection and isolation of the final product," *Nucl. Acids Res.* 12(11):4539–4557 (1984).

Southern et al., "Analyzing and comparing nucleic acid sequences by hybridization to arrays of oligonucleotides: Evaluation using experimental models," *Genomics*, 13:1008–1017 (1992).

Spatola, "Structure–activity relationships of enkaphalins containing serially replace thiomethylene amide bond surrogates," *Life Sci*, 38:1243–1249 (1986).

Sproat et al., "Solid–phase synthesis of oligodeoxyribonucleotides by the phosphotriester method," Chapter 4 in *Oligonucleotide Synthesis: A practical approach*, Gait, ed., IRL Press: Washington, D.C., pp. 83–115 (1984).

Szelke, "Enzyme Inhibitors,"*Chemical Abstracts, American Chemical Society*, 97:39405p (1982).

Tuckerman et al., "Microcapillary thermal interface technology for VLSI packaging," in 1983 Symposium on VLSI Technology, *IEEE* Cat. No. 83:60–61 (1983).

Veber et al., "The design of metabolically–stable peptide analogs," *TINS*, 8:392–396 (1985).

Verlaan–de Vries et al., "A dot–blot screening procedure for mutated ras oncogenes using synthetic oligodeoxynucleotides," *Gene*, 50:313–320 (1986).

\* cited by examiner

FIG. 19
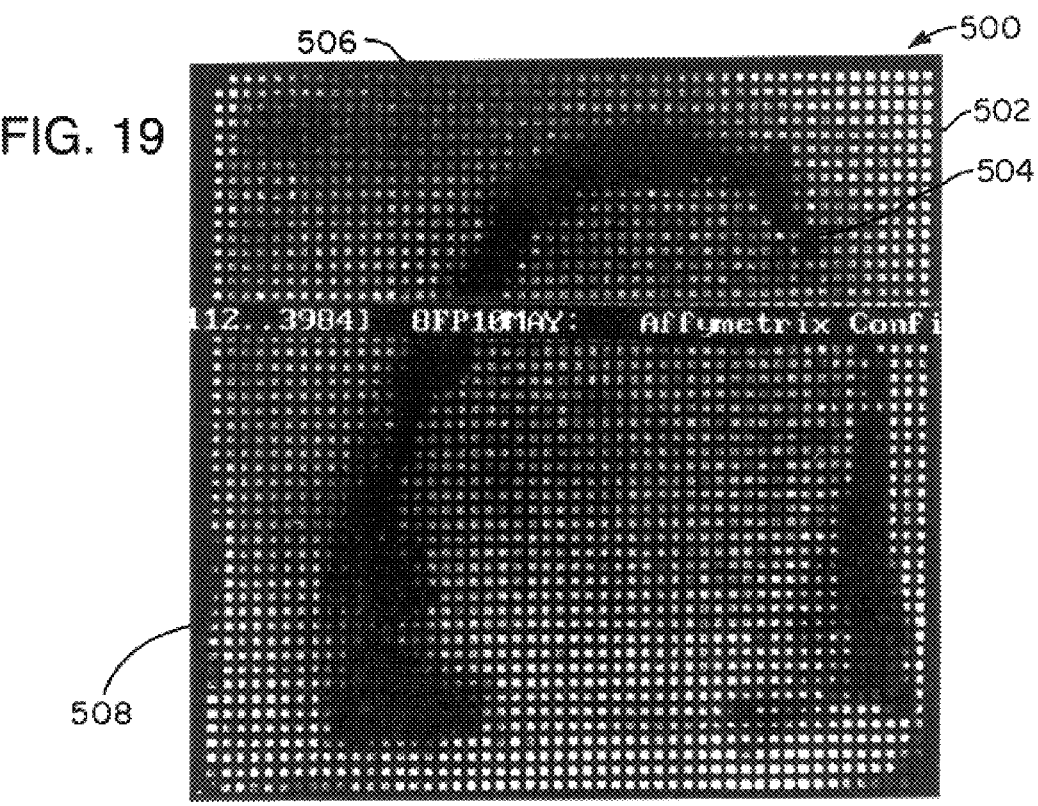
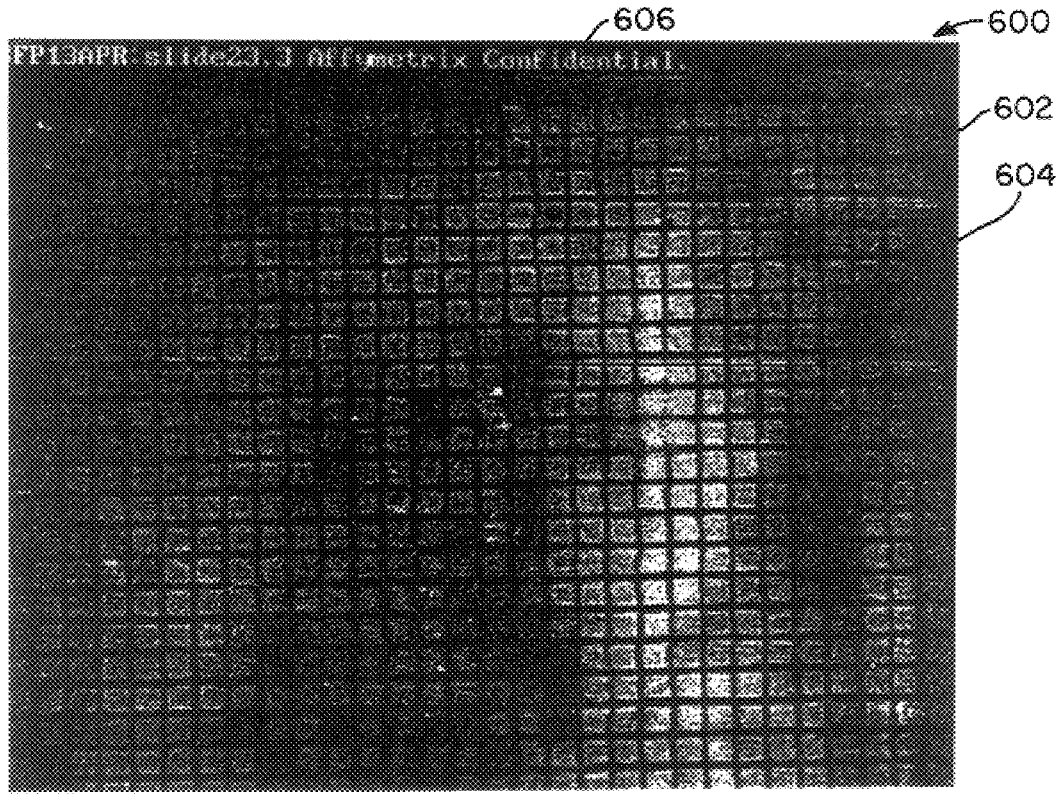
FIG. 20

US 6,667,394 B2

PRINTING OLIGONUCLEOTIDE ARRAYS

This application is a continuation of U.S. patent application Ser. No. 09/427,850, filed Oct. 26, 1999, now U.S. Pat. No. 6,239,273; which in turn is a continuation of U.S. patent application Ser. No. 09/093,843, filed May 22, 1998, now abandoned; which in turn is a continuation of U.S. patent application Ser. No. 08/635,272, filed Apr. 19, 1996, now U.S. Pat. No. 5,831,070; which in turn is a continuation of U.S. patent application Ser. No. 08/395,604, filed Feb. 27, 1995, now U.S. Pat. No. 5,599,695.

BACKGROUND OF THE INVENTION

The present invention relates to the synthesis and placement of materials at known locations. In particular, one embodiment of the invention provides a method and associated apparatus for the selective application of an array of oligonucleotides on a substrate by way of standard dimethoxytrityl (DMT) based chemistry. The invention may be applied in the field of preparation of an oligomer, a peptide, a nucleic acid, an oligosaccharide, a phospholipid, a polymer, or a drug congener preparation, especially to create sources of chemical diversity for use in screening for biological activity.

Industry utilizes or has proposed various techniques to synthesize arrays of oligonucleotides. One such technique is the use of small rubber tubes as reaction chambers to make up a single dimensional array by the sequential addition of reagents. This technique has advantages by the use of standard DMT based chemistry. However, a limitation with resolution often exists with such technique. Typically the smallest cell size is about 1 millimeter in dimension. This method also does not enable the synthesis of a sufficiently large number of polymer sequences for effective economical screening. A further limitation is an inability to form an array of, for example, oligonucleotides at selected regions of a substrate.

Other representative techniques are described in U.S. Pat. No. 5,143,854 and WO93/09668 which is hereby incorporated by reference for all purposes. Such techniques are finding wide use and are considered pioneering in the industry. In some applications, however, it is desirable to have alternative techniques and chemistries for synthesis of compound libraries.

It would be desirable to have a method and apparatus for making high density arrays of oligonucleotides using DMT-based chemistry and other suitable oligonucleotide synthesis chemistries, as is a method and apparatus for conventional phosphoramidite-based synthesis of a spatially defined array of oligomers (e.g., polynucleotides, polypeptides, oligosaccharides, and the like) each having a substantially predetermined sequence of residues (i.e., polymerized monomer units).

SUMMARY OF THE INVENTION

According to the present invention, a method and apparatus to form an array of polymers, such as oligonucleotides and a substrate using conventional linkage chemistries (e.g., standard DMT-based oligonucleotide synthesis chemistry) is provided. The method and apparatus includes use of selected printing techniques in distributing materials such as barrier materials, deprotection agents, base groups, nucleosides, nucleotides, nucleotide analogs, amino acids, imino acids, carrier materials, and the like to selected regions of a substrate. Each of the printing techniques may be used in some embodiments with, for example, standard DMT-based chemistry for synthesis of oligonucleotides, and in particular selected deprotecting agents in vapor form.

In a specific embodiment, the present invention provides a method of forming polymers having diverse monomer sequences on a substrate. In an embodiment, the method is used to synthesize oligonucleotides having predetermined polynucleotide sequence(s) on a solid substrate, typically in the form of a spatially defined array, wherein the sequence(s) of an oligonucleotide is positionally determined. The present method includes steps of providing a substrate with a linker molecule layer thereon. The linker molecule layer has a linker molecule and a protective group. The present method also includes a step of applying a barrier layer overlying at least a portion of the linker molecule layer. The barrier layer shields the underlying portion from contact with a reagent capable of otherwise reacting with the underlying portion and applied subsequent to application of the barrier layer, thereby substantially precluding a predetermined chemical reaction from occurring on areas of the substrate overlaid with the barrier material. The applying step forms selected exposed regions of the linker molecule layer. A step of exposing the selected exposed regions of the linker molecule layer (e.g., regions not overlaid with the barrier material) to a reagent, typically in vapor phase, and often comprising a deprotecting agent is also included.

In an alternative specific embodiment, the present method includes a method of applying a medium in selected regions of a substrate. The present method includes steps of providing a substrate with a top surface, and selectively applying a medium having an element selected from a group consisting of a barrier material, a receptor, a deprotection agent, a monomer group, a carrier material, and an activator to selected regions of the substrate top surface.

In an embodiment, the invention provides a method for synthesizing a spatial array of polymers of diverse monomeric sequence (e.g., such as a collection of oligonucleotides having unique sequences), wherein the composition (e.g., nucleotide sequence) of each polymer is positionally defined by its location in the spatial array. In general, the method employs a masking step whereby a spatially distributed barrier material is applied to a substrate to block at least one step of a monomer addition cycle from occurring on a portion of the substrate overlaid by the barrier material. The method comprises applying a barrier material to a first spatially defined portion of a substrate, said substrate optionally also comprising a layer of linker molecules and/or nascent polymers (e.g., nascent oligonucleotides), whereby the barrier material overlaying said first spatially defined portion of said substrate shields the underlying portion from contact with a subsequently applied reagent capable of otherwise reacting with the underlying portion and necessary for a complete monomer addition cycle whereby a monomer unit is covalently linked to a nascent polymer or linker, thereby substantially precluding a chemical reaction from occurring on said first spatially defined portion which is overlaid with the barrier material and providing a remaining unshielded portion of said substrate (i.e., portion(s) not overlaid with the barrier material) available for contacting said subsequently applied reagent and undergoing said chemical reaction necessary for a complete monomer addition cycle (i.e., polymer elongation). The subsequently applied reagent is typically a monomer (e.g., nucleotide, nucleoside, nucleoside derivative, amino acid, and the like), a deprotecting agent for removing protecting group(s) which block polymer elongation (e.g., removal of DMT groups by acid hydrolysis), a coupling agent (e.g., phosphoramidites, such as cyanoethyl phosphoramidite nucleosides), a capping agent (e.g., acetic anhydride and 1-methylimidazole), and/or an oxidation agent (e.g., iodine; such as in iodine:water:pyridine:tetrahydrofuran mixture). The method further provides that, subsequent to the application of the barrier material, the reagent(s) is/are applied and permitted to chemically react with the unshielded portion of the substrate for a suitable time period and under suitable reaction conditions. Following reaction of the unshielded portion with the reagent(s), monomer addition is completed and the barrier material is removed (not necessarily in that order), resulting in a monomer addition to polymer(s) in the unshielded portion of the substrate and substantial lack of monomer addition to polymer(s) in the shielded portion of the substrate, during said monomer addition cycle.

In an embodiment, the masking step, wherein a barrier material is applied to a spatially defined portion of the substrate and used to shield said spatially defined portion to block a monomer addition cycle on said spatially defined portion, is employed repetitively. A first barrier mask is applied to overlay a first spatially defined portion of a substrate creating: (1) a first shielded portion overlain by said barrier mask, and (2) a first unshielded portion comprising the portion of the substrate not overlain by said barrier mask. The application of the first barrier mask is followed by completion of a first monomer addition cycle, whereby a monomer unit is covalently added to the first unshielded portion to extend or initiate a nascent polymer bound to said substrate, typically covalently, and whereby said first monomer addition cycle substantially fails to result in addition of a monomer unit to nascent polymers in the first shielded portion. The first barrier mask is removed, concomitant with, prior to, or subsequent to the completion of said first monomer addition cycle, and one or more subsequent cycles of applying a subsequent barrier mask, which may overlay subsequent shielded portions which is/are spatially distinct from said first shielded portion, and performing at least one subsequent monomer addition cycle(s) followed after each cycle by barrier removal, and optionally, reapplication of a barrier mask and initiation of a further monomer addition cycle until polymers of a predetermined length (number of incorporated monomer units) are produced.

In an aspect of the invention, a repetitive masking/synthesis process can be comprised of the following steps:

(1) application of barrier material to substrate having a reactive surface capable of covalently bonding to a monomer unit or reacting with a deprotecting agent or other reagent necessary for completion of a monomer addition cycle, said reactive surface being derivatived with a linker and/or a monomer unit or nascent polymer (e.g., a 3'-linked nucleoside or 3'-linked polynucleotide), wherein said barrier material covers a portion of said reactive surface creating a covered portion, said covered portion being a shielded portion and being substantially incapable of reacting with a monomer unit or reagent necessary for completion of a monomer addition cycle, and the remaining portion of the substrate being an unshielded portion capable of reacting with a monomer unit or reagent necessary for completion of a monomer addition cycle;

(2) contacting the substrate with reagents necessary for completion of a monomer addition cycle, wherein a monomer unit is covalently attached to the reactive surface of the substrate (e.g., a linker, a 3'-linked nucleoside, or 3'-linked nascent polynucleotide) in an unshielded portion;

(3) removing the barrier material; and (4) repeating steps 1, 2, and 3 from 0 to 5000 cycles, preferably from 2 to 250 cycle, more usually from 4 to 100 cycles, and typically from about 7 to 50 cycles, until a predetermined polymer length is produced on a portion of the substrate. The pattern of barrier material applied in each cycle may be different that the prior or subsequent cycle(s), if any, or may be the same. Often, in step (2), at least one reagent necessary for completion of a monomer addition cycle is applied in vapor phase.

In an embodiment of the invention is provided a substrate having a spatial array of polymers of predetermined length produced by the method described supra.

In one aspect of the invention is provided a method for applying a barrier material or reagent necessary for a monomer addition cycle to a substrate, said method comprising transferring the barrier material or reagent as a charged droplet by electrostatic interaction, such as, for example, in an inkjet or bubble jet print head or similar device. In an embodiment, the barrier material or reagent is suitable for use in polynucleotide (oligonucleotide) synthesis. In an embodiment, the substrate is a silicon or glass substrate or a charged membrane (e.g., nylon 66 or nitrocellulose).

An aspect of the invention provides a method for synthesizing polynucleotides on a substrate, said method comprising application of at least one reagent necessary for addition of a nucleotide to a nascent polynucleotide or linker molecule bound to a substrate, wherein said application is performed with the reagent present substantially in vapor phase.

A further understanding of the nature and advantages of the present invention may be realized by reference to the latter portions of the specification and attached drawings.

BRIEF DESCRIPTION OF THE DRAWINGS

FIG. 19 illustrates a SEM photograph of a 100 micron resolution sample with an epoxy barrier pattern;

FIG. 20 illustrates a SEM photograph of a 75 micron resolution sample with an epoxy barrier pattern;

DESCRIPTION OF THE SPECIFIC EMBODIMENT

Glossary

Figure 1:
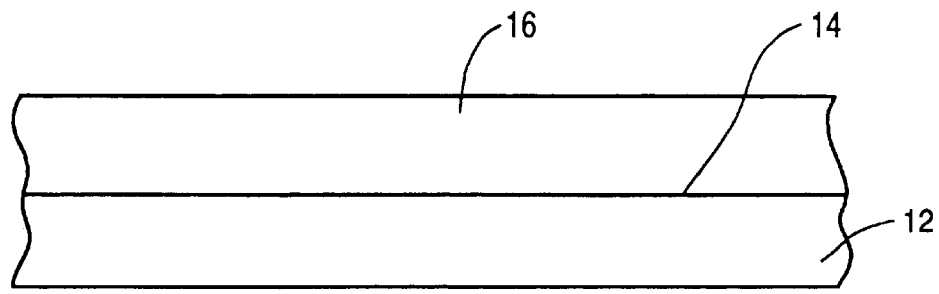
FIGS. 1–3 illustrate simplified cross-sectional views of a substrate being processed according to the present invention.

The following terms are intended to have the following general meanings as they are used herein:

1. Ligand: A ligand is a molecule that is recognized by a particular receptor. Examples of ligand that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides, nucleic acids, oligosaccharides, proteins, and monoclonal antibodies.

2. Monomer: A member of the set of small molecules which are or can be joined together to form a polymer. The set of monomers includes but is not restricted to, for example, the set of common L-amino acids, the set of D-amino acids, the set of synthetic and/or natural amino acids, the set of nucleotides and the set of pentoses and hexoses. The particular ordering of monomers within a polymer is referred to herein as the "sequence" of the polymer. As used herein, monomers refers to any member of a basis set for synthesis of a polymer, which include for example and not limitation, polynucleotides, polypeptides, and small molecules such as benzodiazepines, β-turn mimetics, and protoprostaglandins, among others. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as amino acids, but could readily be applied in the preparation of other polymers. Such polymers include, for example, both linear and cyclic polymers of nucleic acids, polysaccharides, phospholipids, and peptides having either α-, β-, OR ω-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in application Ser. No. 07/796,727 filed Nov. 22, 1991 (now U.S. Pat. No. 5,242,974 issued Sep. 7, 1993, entitled "POLYMER REVERSAL ON SOLID SURFACES," incorporated herein by reference for all purposes. One set of polymers is polynucleotides and peptide nucleic acids.

3. Peptide: A polymer in which the monomers are alpha amino acids and which are joined together through amide bonds, alternatively referred to as a polypeptide. In the context of this specification it should be appreciated that the amino acids may be the L-optical isomer or the D-optical isomer. Peptides are often two or more amino acid monomers long, and often more than 20 amino acid monomers long. Standard abbreviations for amino acids are used (e.g., P for proline). These abbreviations are included in Stryer, *Biochemistry,* Third Ed., 1988, which is incorporated herein by reference for all purposes. Peptide analogs are commonly used in the pharmaceutical industry as non-peptide drugs with properties analogous to those of the template peptide. These types of non-peptide compound are termed "peptide mimetics" or "peptidimimetics" (Fauchere, J. (1986) Adv. Drug Res. 15:29; Veber and Freidinger (1985) *TINS* p.392; and Evans et al. (1987) *J. Med. Chem* 30: 1229, which are incorporated herein by reference) and are often developed with the aid of computerized molecular modeling. Peptide mimetics that are structurally similar to therapeutically useful peptides may be used to produce an equivalent therapeutic or prophylactic effect. Generally, peptidomimetics have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—CH$_2$NH—, CH$_2$CH$_2$—); Spatola, A. F. et al., *Life Sci* (1986) 38:1243–1249 (—CH$_2$—S); Hann, M. M.,*J Chem Soc Perkin Trans I* (1982) 307–314 (—CH—CH—, cis and trans); Almquist, R. G. et al., *J Med Chem* (1980) 23:1392–1398 (—COCH$_2$—); Jennings-White, C. et al., *Tetrahedron Lett* (1982) 23:2533 (—COCH$_2$—); Szelke, M. et al., European Appln. EP 45665 (1982) CA: 97:39405 (1982) (—CH(OH)CH$_2$—); Holladay, M. W. et al., *Tetrahedron Lett* (1983) 24:4401–4404 (—C(OH)CH$_2$—); and Hruby, V. J., *Life Sci* (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

4. Receptor: A molecule that has an affinity for a given ligand. Receptors may be naturally-occurring or man-made molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Specific examples of receptors which can be investigated by this invention include but are not restricted to:

a) Microorganism receptors: Determination of ligands which bind to receptors, such as specific transport proteins or enzymes essential to survival of microorganisms, is useful in a new class of antibiotics. Of particular value would be antibiotics against opportunistic fungi, protozoa, and those bacterial resistant to the antibiotics in current use.

b) Enzymes: For instance, the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or led to the development of related diagnostic agents or compounds useful in therapeutic treatments such as for auto-immune diseases (e.g., by blocking the binding of the "self" antibodies).

d) Nucleic Acids: Sequences of nucleic acids may be Polynucleotides, which include oligonucleotides, are composed of nucleotides, typically linked 5' to 3' by a phosphodiester bond or phosphorothiolate bond or the like.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA". Polynucleotides can include nucleotides having a variety of bases, including but not limited to: adenine, thymine, cytosine, guanine, uridine, inosine, deazaguanosine, $N^2$-dimethylguanosine, 7-methylguanosine, $N^6$-$\Delta^2$ isopentenyl-2-methylthioadenosine, 2'-O-methyladenine, 2'-O-methylthymine, 2'-O-methylcytosine, 2'-O-methylguanine, pseudouridine, dihydrouridine, 4-thiouridine, and the like.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone Receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. other examples are the vasoconstrictive hormone receptore; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

5. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis. Often, the substrate is a silicon or glass surface, or a charged membrane, such as nylon 66 or nitrocellulose.

6. Protective Group: A material which is bound to a monomer unit and which may be selectively removed therefrom to expose an active site such as, in the specific example of an amino acid, an amine group. In the specific example of a polynucleotide synthesized via phosphoramidite chemistry, a protecting group can be a trityl ether (DMT ether) group linked to a nucleotide via a 5'-hydroxyl position.

7. Predefined Region: A predefined region is a localized area on a substrate which is, was, or is intended to be used for formation of a selected polymer and is otherwise referred to herein in the alternative as a "selected" region or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 cm$^2$, more preferably less than 1 mm$^2$, still more preferably less than 0.5 mm$^2$, and in some embodiments about 0.125 to 0.5 mm$^2$. In most preferred embodiments the regions have an area less than about 10,000 $\mu$m$^2$ or, more preferably, less than 100 $\mu$m$^2$. Within these regions, the polymer synthesized therein is preferably synthesized in a substantially pure form. A shielded portion or unshielded portion can be a predefined region.

8. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. such characteristics will typically be measured by way of binding with a selected ligand or receptor. Preferably the region is sufficiently pure such that the predominant species in the predefined region is the desired sequence. According to preferred aspects of the invention, the polymer is 5% pure, more preferably more than 10% pure, preferably more than 20% pure, and more preferably more than 80% pure, more preferably more than 90% pure, more preferably more than 95% pure, where purity for this purpose refers to the ratio of the number of ligand molecules formed in a predefined region having a desired sequence to the total number of molecules formed in the predefined region.

9. Monomer Addition Cycle: A monomer addition cycle is a cycle comprising the chemical reactions necessary to produce covalent attachment of a monomer to a nascent polymer or linker, such as to elongate the polymer with the desired chemical bond (e.g., 5'-3' phosphodiester bond, peptide bond, etc.). For example and not to limit the invention, the following steps typically comprise a monomer additon cycle in phosphoramidite-based oligonucleotide synthesis: (1) deprotection, comprising removal of the DMT group from a 5'-protected nucleoside (which may be part of a nascent polynucleotide) wherein the 5'-hydroxyl is blocked by covalent attachment of DMT, such deprotection is usually done with a suitable deprotection agent (e.g., a protic acid: trichloroacetic acid or dichloroacetic acid), and may include physical removal (e.g., washing, such as with acetonitrile) of the removed protecting group (e.g., the cleaved dimethyltrityl group), (2) coupling, comprising reacting a phosphoramidite nucleoside(s), often activated with tetrazole, with the deprotected nucleoside, (3) optionally including capping, to truncate unreacted nucleosides from further participation in subsequent monomer addition cycles, such as by reaction with acetic anhydride and N-methylimidazole to acetylate free 5'-hydroxyl groups, and (4) oxidation, such as by iodine in tetrahydrofuran/water/pyridine, to convert the trivalent phosphite triester linkage to a pentavalent phosphite triester, which in turn can be converted to a phosphodiester via reaction with ammonium hydroxide. Thus, with respect to phosphoramidite synthesis of polynucleotides, the following reagents are typically necessary for a complete monomer addition cycle: trichloroacetic acid or dichloroacetic acid, a phosphoramidite nucleoside, an oxidizing agent, such as iodine (e.g., iodine/water/THF/pyridine), and optionally N-methylimidazole for capping.

10. Specific hybridization is defined herein as the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially identical to the target polynucleotide. However, it will be recognized by those of skill that the minimum length of a polynucleotide required for specific hybridization to a target polynucleotide will depend on several factors: G!C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

General

The present invention provides for the use of a substrate with a surface. In preferred embodiments, linker molecules are provided on a surface of the substrate. The purpose of the linker molecules, in certain embodiments, is to facilitate receptor recognition of the synthesized polymers. In preferred embodiments, the linker molecules each include a protection group. A layer of barrier material may be applied to the surface of the substrate, and in particular the linker molecule layer. The barrier material is selectively applied by way of a variety of printing techniques to form exposed regions. A step of deprotection by way of deprotection agents may then be applied to the exposed regions. Preferably, the deprotection step occurs with use of deprotection agents in the vapor phase. This sequence of steps may be used for the selected synthesis of an array of oligonucleotides.

The present invention also provides for use of selected printing techniques to apply deprotection agents, barrier materials, nucleosides, and the like for the synthesis of an array of oligonucleotides. Preferably, the type of printing technique should be able to transfer a sufficient volume of print material to selected regions of the substrate in an easy, accurate, and cost effective manner. Examples of various printing techniques for the synthesis of for example an array of oligonucleotides are described herein. Further examples of these embodiments of the present invention may be applied to the synthesis of arrays of DNA as explained by application Ser. No. 07/796,243 in the name of Winkler et al., and U.S. Pat. No. 5,143,854 in the name of Pirrung et al., which are both hereby incorporated by reference for all purposes.

Examples of suitable phosphoramidite synthesis methods are described in the User Manual for Applied Biosystems Model 391, pp. 6–1 to 6–24, available from Applied Biosystems, 850 Lincoln Center Dr., Foster City, Calif. 94404, and are generally known by those skilled in the art.

Chemical synthesis of polypeptides is known in the art and are described further in Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins,* Wiley Publishing, which are incorporated herein by reference).

Once synthesized, polynucleotide arrays of the invention have many art-recognized uses. For example and not limitation, the synthesized sequences may be used as hybridization probes or PCR amplimers to detect the presence of a specific DNA or mRNA, for example to diagnose a disease characterized by the presence of an elevated mRNA level in cells, to identify a disease allele, or to perform tissue typing (i.e., identify tissues characterized by the expression of a particular mRNA), and the like. The sequences may also be used for detecting genomic gene sequences in a DNA sample, such as for forensic DNA analysis (e.g., by RFLP analysis, PCR product length(s) distribution, etc.) or for diagnosis of diseases characterized by amplification and/or rearrangements of a characteristic gene.

Embodiments of the Present Invention

An embodiment of the present invention may be briefly outlined by way of the following method.

1. Provide a substrate.
2. Optionally, form a layer of linker molecules on the substrate.
3. Mechanically apply a barrier pattern on the linker molecules with exposed regions.
4. Deprotect the linker molecules in the exposed regions with standard DMT chemistry.
5. Strip barrier pattern.
6. Apply remaining synthesis steps.

This sequence of steps provides for an embodiment with use of a barrier layer with standard DMT chemistry. This provides for a desired selectivity, easy in synthesis, low costs, high contrast, high resolution, among other features. Of course, this sequence of steps is shown for illustrative purposes only, and should not limit the scope of the appended claims herein.

An alternative embodiment of the present invention may be briefly outlined by way of the following method.

1. Provide a substrate.
2. Optionally, form a layer of linker molecules on the substrate.
3. Selectively apply a print media by way of a printing technique (not a photosensitive printing techniques) on the linker molecules.
4. Apply remaining synthesis steps.

This sequence of steps allows for the selective application of a print medium onto a substrate by way of the various printing techniques described herein. These printing techniques simply do not use any exotic photosensitive type materials, although later photosensitive steps can be combined with the teachings herein. In preferred embodiments, deprotection agents may be introduced onto the substrate in vapor form. Accordingly, the present invention provides for the selective application of a variety of print media onto a substrate without necessitating the use of conventional photosensitive materials.

FIG. 1 illustrates one embodiment according to the present method. A substrate 12 is shown in cross-section. The substrate may be biological, nonbiological, organic, inorganic, or a combination of any of these, existing as particles, strands, precipitates, gels, sheets, tubing, spheres, containers, capillaries, pads, slices, films, plates, slides, and the like. The substrate may have any convenient shape, such as a disc, square, sphere, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. For instance, the substrate may be a functionalized glass, Si, Ge, GaAs, GaP, $SiO_2$, $SiN_4$, modified silicon, or any one of a wide variety of gels or polymers such as (poly) tetrafluoroethylene, polypropylene, polyethylene, (poly) cinylidenedifluoride, poly-styrene, polycarbonate, or combinations thereof. Other substrate materials will be readily apparent to those of skill in the art upon review of this disclosure. In a preferred embodiment the substrate is flat glass or single-crystal silicon with surface relief features of less than 10 microns. In another preferred embodiment, the substrate is a polypropylene material.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which could be carboxyl, amino, hydroxyl, or the like. Most preferably, the surface will have surface Si—OH functionalities, such as are found on silica surfaces. For synthesis of polynucleotides by phosphoramidite chemistry, a linker consisting of (—COCH2CH2CONHCH2CH2CH2— siloxane bond-glass substrate) may be used to attach to a DMT-protected nucleoside via formation of a carboxyl bond to the 3' hydroxyl of the nucleoside.

The substrate 12 includes a surface 14 with a layer of linker (or spacer) molecules 16 thereon. The linker molecules are preferably of sufficient length to permit polymers in a completed substrate to interact freely with molecules exposed to the substrate. The linker molecules should be about 4 to about 40 atoms long to provide sufficient exposure. The linker molecules may be, for example, aryl acetylene, ethylene glycol oligomers containing 2–10 monomer units, diamines, diacids, amino acids, among others, and combinations thereof. Alternatively, the linkers may be the same molecule type as that being synthesized (i.e., nascent polymers), such as oligonucleotides or oligopeptides.

In a preferred embodiment, the linker molecules are PEG linker. Of course, the type of linker molecules used depends upon the particular application.

The linker molecules can be attached to the substrate via carbon—carbon bonds using, for example, (poly) trifluorochloroethylene surfaces, or preferably, by siloxane bonds (using, for example, glass or silicon oxide surfaces). Siloxane bonds with the surface of the substrate may be formed in one embodiment via reactions of. linker molecules bearing trichlorosilyl groups. The linker molecules may optionally be attached in an ordered array, i.e., as parts of the head groups. In alternative embodiments, the linker molecules are absorbed to the surface of the substrate.

The linker molecules or substrate itself and monomers used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating.

In a subsequent step, the substrate 12 includes a barrier pattern 18 with selected exposed regions 20 formed thereon. Each of the exposed regions corresponds to an "opening" in the barrier material where it is desirable to remove protecting groups from the linker molecules. The protecting groups may be removed from the linker molecules by immersion in the deprotecting solution. Examples of the deprotecting solution include trichloroacetic acid, hydrochloric acid, among others.

The barrier pattern can be made of any suitable material capable of masking certain regions of the linker molecule layer to protect such regions from subsequent processing. The barrier pattern may include, for example, materials such as a lacquer, an oil, a mask stencil, a silicone mask, an epoxy, a silicone oil, a polyester, a silicon membrane mask, a liquid capable of providing a barrier to protecting groups, a solid capable of providing a barrier to protecting groups, among others, and combinations thereof. The lacquer may include a lacquer such as Pactra 63-1 and others, often having characteristics formulated to withstand hot fuel. An epoxy may include any suitable epoxy type material such as West 105 and others. Selected oils are a rotary pump oil such as Mowioc MC110, a silicone oil such as Dow Corning 704, and others. Polyester type materials may include TAP SB and the like, and combinations thereof.

The barrier pattern is applied as a liquid or a vapor by a variety of techniques. Examples of selected ways to apply the barrier material include brush, spray techniques, selected printing techniques, and others.

Selected printing techniques may be used for the application of liquid barrier materials. The selected techniques of printing include a relief or letter press (the oldest form), gravure or intaglio. stencil printing, lithography, among others. FIGS. 4–17, which will be described in more detail below, illustrate a variety of printing techniques used in applying the barrier material. Some of the techniques as applied in the printing industry were from Printing Technology, J. Michael Adams, David D. Faux, Lloyd J. Ricker (3d.Ed., Delmar, 1988), which is hereby incorporated by reference for all purposes.

Figure 2:
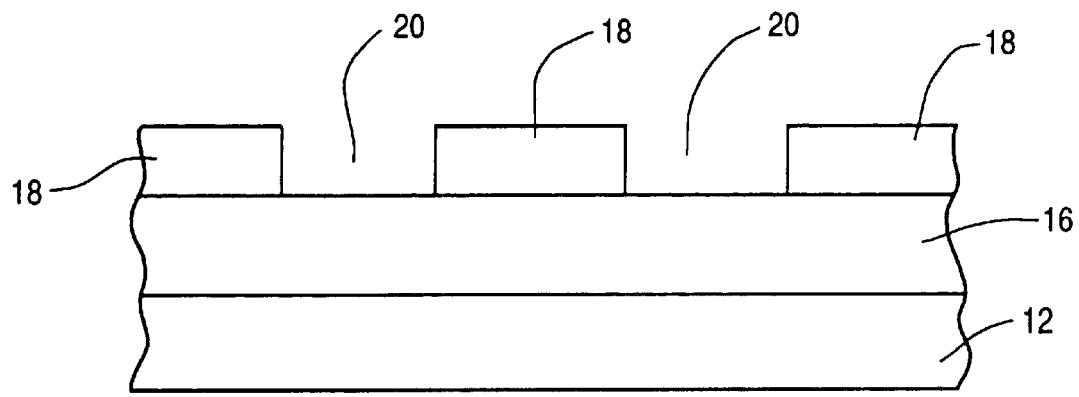
Figure 3:
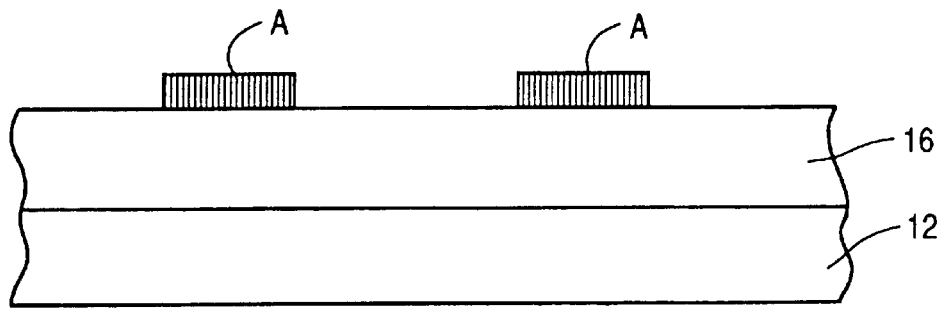
Figure 4:
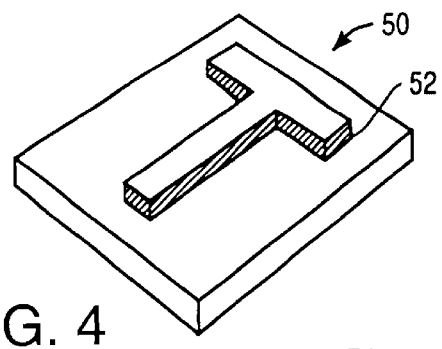
FIGS. 4–13 illustrate selected printing techniques according to the present invention.
Figure 5:
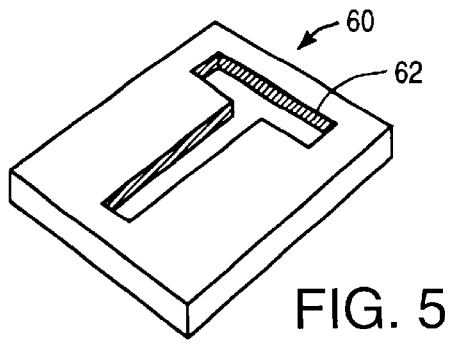
Figure 6:
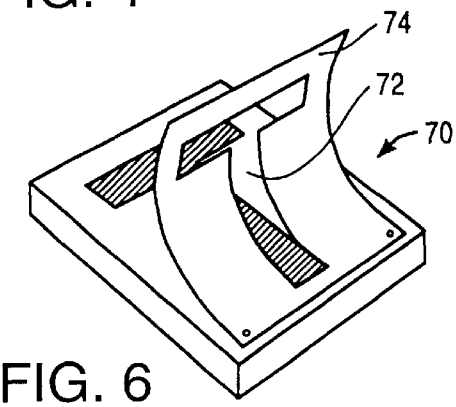
Figure 7:
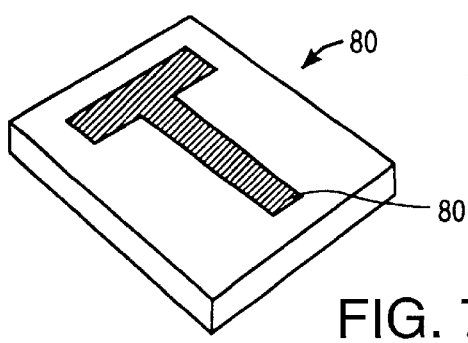

After optionally deprotecting the linker molecule layer, the barrier material is then stripped by methods of wet chemical strip, acetone, IPA, and others. The linker molecule layer is then washed or otherwise contacted with a first monomer layer such as receptor "A" in FIG. 3. The first monomer reacts with the activated functional groups of the linker molecules which have been deprotected. FIG. 3 illustrates a simplified cross-sectional diagram of the substrate 12, linker molecule layer 12, and monomer layer "A." The sequence of steps illustrated by FIGS. 1–3 may be repeated to achieve the desired sequence of monomers at selected regions to form an array of oligonucleotides, peptides, other polymers, and the like.

FIGS. 4–7 illustrate techniques of printing as relief or letter press 50, gravure or intaglio 60, stencil printing 70, and lithography 80, respectively. Relief printing 50 relies upon the use of raised features 52 to transfer printing medium to a substrate. As for Gravure or intaglio printing 60, it uses sunken features 62 to apply the desired shape to a substrate. Stencil printing 70 which includes screen printing, shadow masking, spray painting, and others, occurs through mechanical openings 72 of a stencil 74. Lithography is a form of printing regions 82 of a surface that are chemically treated to selectively retain print medium. Each of these techniques may be used for the application of a barrier material, a carrier material, a deprotecting agent, or a polymer unit pattern onto a substrate.

More recent forms of printing include xerography (which includes laser printing), ink jet printing (or print medium jet printing), and others. FIGS. 8–13 illustrate the more recent forms of printing.

Figure 8:
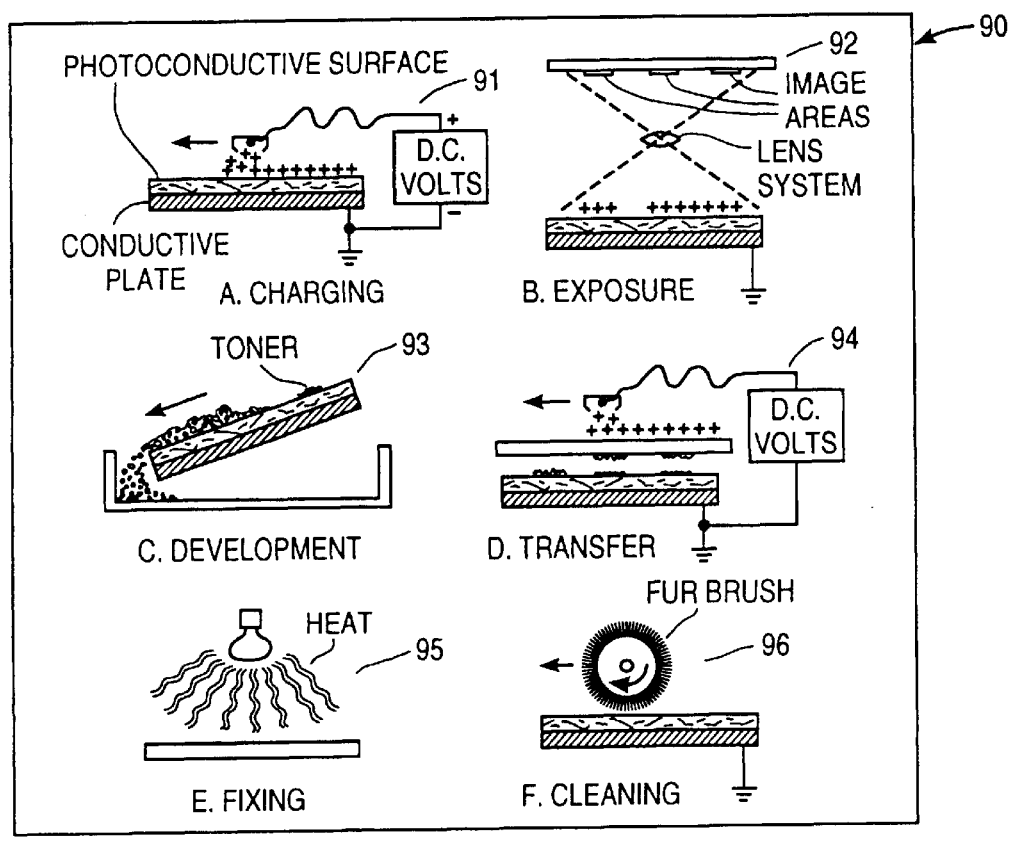

FIG. 8 illustrates a form of xerography printing 90. Xerography printing is directed to printing by way of an electrical charge pattern. Steps of xerography printing often include steps of charging 91, exposure 92, development 93, transfer 94, fixing 95, and cleaning 96.

Figure 9:
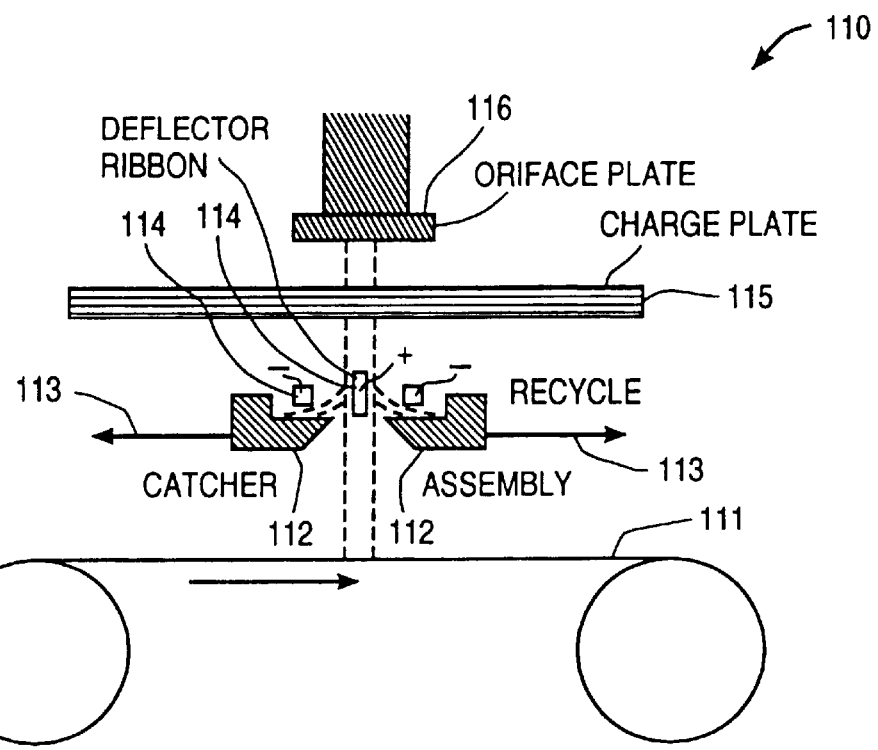
Figure 10:
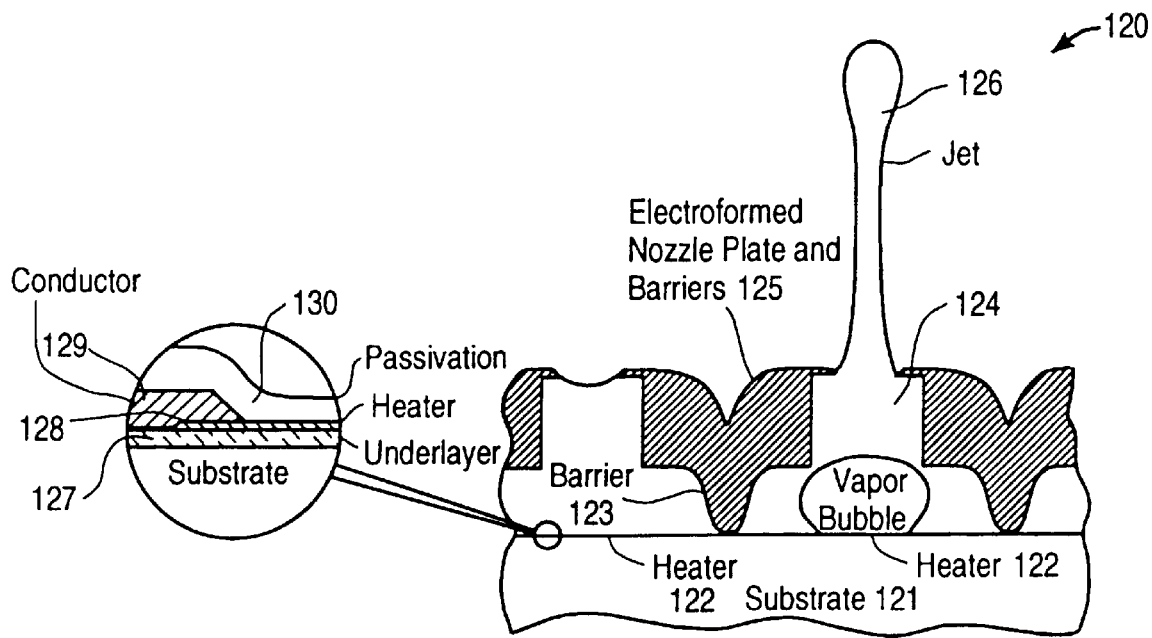

FIG. 9–10 illustrates two forms of printing known as ink jet printing or in this case print medium jet printing. In this type of printing, print medium is forced through an array of orifices that is scanned across a workpiece, and is therefore really a form or derivative of stencil printing. FIG. 9 illustrates a continuous ink jet process 110. The continuous print medium jet process includes a substrate 111, a catcher assembly 112, a recycle 113, a deflector ribbon 114, a charge plate 115, an orifice plate 116, among other elements. The print medium jet type printer may deliver a pattern of selected print medium in a single pass. A resolution of such printing technique can be as low as about 200 microns and less.

The printhead includes a substrate 121, a heater assembly 122, a barrier 123, print medium 124, a nozzle plate 125, and the print medium jet 126. The heater assembly 122 may be formed from a underlayer 127 overlying the substrate, a resistive heater element 128 overlying the underlayer, a conductor 129, and a overlying layer of passivation 130. The drop-on-demand printhead has the capability of delivering controlled amounts of fluids such as barrier medium, carrier material, monomer units, and the like onto the surface of a workpiece.

Figure 11:
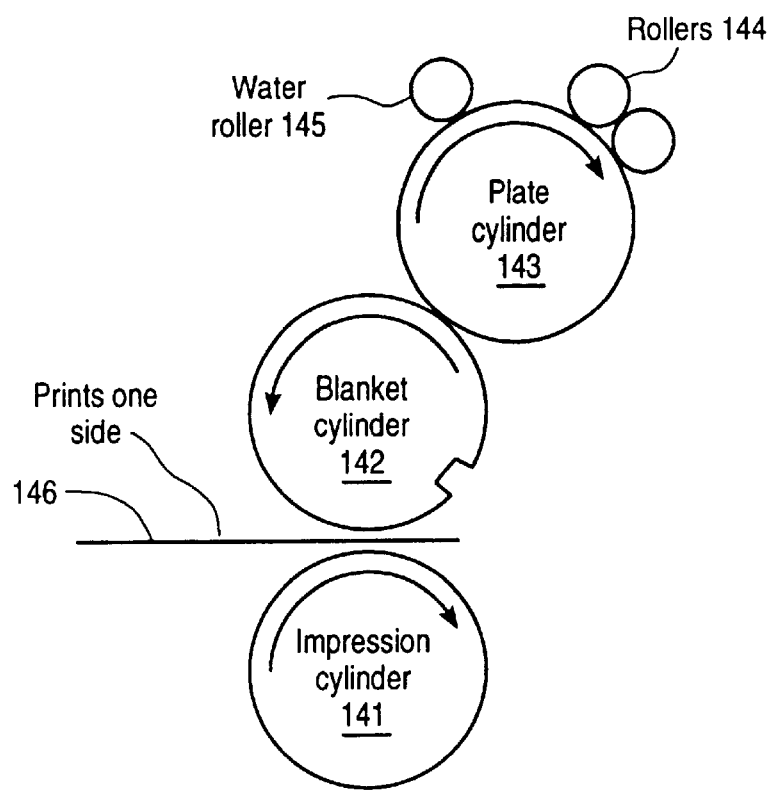

A simplified cross-sectional view of an offset rotary press 140 is illustrated by FIG. 11. The offset rotary press includes a impression cylinder 141, a blanket cylinder 142, a plate cylinder 143, print medium rollers 144, a solvent roller 145, and a substrate 146. The image is transferred (or offset) from the plate cylinder to the blanket cylinder, which reverses the image. The image is then passed to the press substrate (or sheet) as it moves between the blanket cylinder and the impression cylinder.

Figure 12:
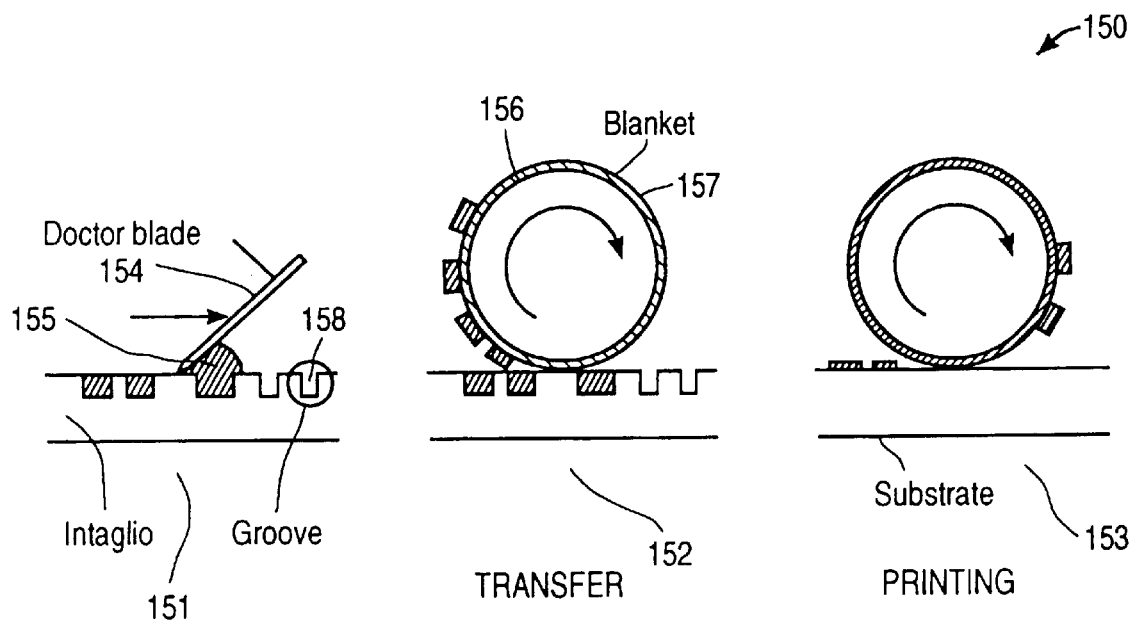

Another form of offset printing such as gravure offset printing 150 is illustrated by FIG. 12. Gravure offset printing includes steps of print medium transfer 151, transfer 152, and printing 153. A doctor blade 154 may be used to force medium 155 into grooves 158 during the print medium transfer step. The print medium is then transferred onto a blanket cylinder 156, often covered with a rubber blanket 157. The blanket cylinder then prints the print medium onto a substrate. An example of gravure offset printing is illustrated in Mikami et al., IEEE Transactions on Electron Devices 41, 306, (March 1994), which is hereby incorporated by reference for all purposes. Mikami et al. applies offset printing for the manufacture of arrays of thin film transistors for flat panel displays. By way of gravure offset printing, features sizes down to about 30 micrometers have been made.

Figure 13:
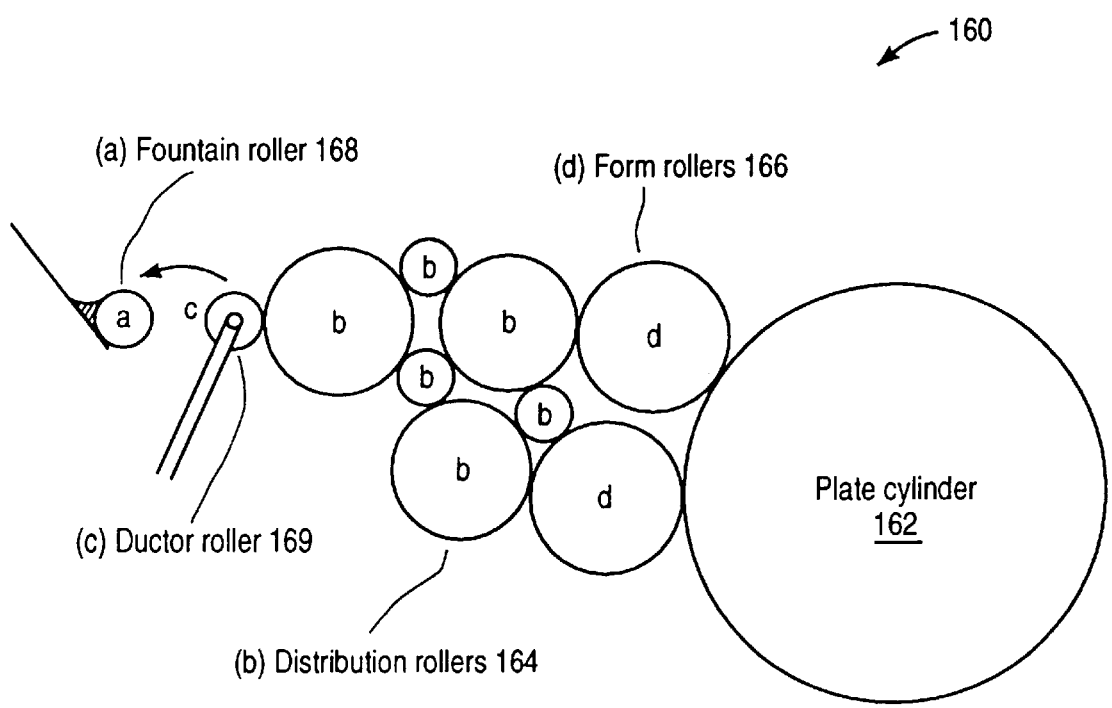

Still a further printing technique 160 is illustrate by FIG. 13. The printing technique includes use of a plate cylinder 162, a plurality of distribution rollers 164, a plurality of form rollers 166, a print medium fountain roller 168, a ductor roller 169, and other elements. This type of technique provides for a more uniform distribution of barrier medium, carrier medium, deprotecting agents or polymer units (or conventional ink) in selected applications.

In preferred embodiments, spatially selectivity and in particular local selectivity is achieved by way of trapping liquid under an in-contact stencil mask. It should be noted that local selectivity refers to the process of forming the liquid barrier at a selected or predefined region. A liquid may attach to solid surfaces and pull them together with selected values of surface and interfacial energies. The pull is characterized as a pressure P in the following relationship:

$$P = T/R$$

where

P is the suction pressure between the two surfaces;

T is the surface tension of the liquid; and

R is the radius of curvature of the meniscus.

The relationship assumes a small contact angle, but not so small as to cause liquid to creep along surfaces of either solid. An example of this technique is illustrated in D. B. Tuckerman and R. F. W. Pease, Paper presented at U.S./Japan VLSI Symposium, Kaanapaali, HI 1983 (Tuckerman et al.), which is hereby incorporated by reference for all purposes. Tuckerman et al. discloses the use of DC 704 oil to attach integrated circuit chips in this manner.

A suitable value for R often requires that the volume of liquid just fills the gap between the solid surfaces of the barrier and substrate. Too little liquid and the gap empties to drain certain regions, thereby creating no deprotection at such regions. Too much liquid corresponds to a larger R, and the reduction of the attractive force P. Of course, the selected amount of liquid depends upon the particular application.

Figure 14:
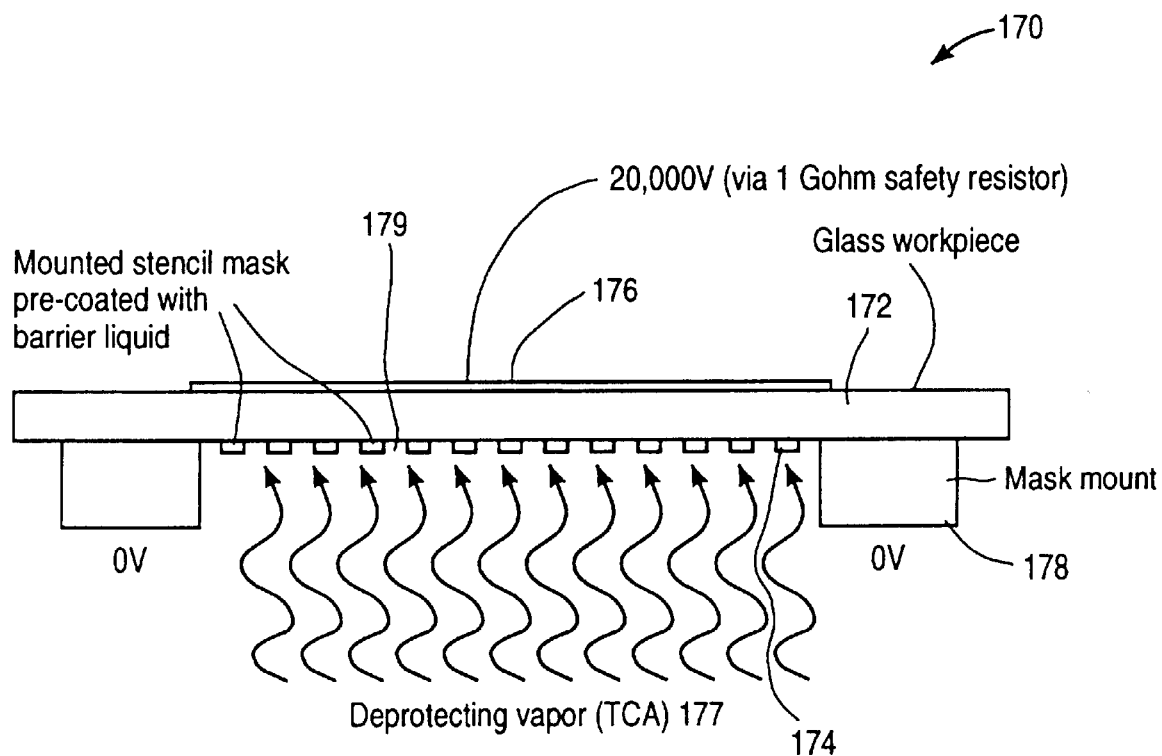
FIG. 14 illustrates a simplified cross-sectional view of an apparatus used to achieve local selectivity.

FIG. 14 illustrates a simplified cross-sectional view of an apparatus 170 used to achieve local selectivity. The apparatus includes a glass workpiece 172, a stencil 174, an upper electrode 176, a mask mount (or lower electrode) 178, and other features. The glass workpiece is positioned between the upper electrode and the mask mount. A voltage such as one of about 20,000 volts is applied to the upper electrode, while the mask mount (or lower electrode includes a potential at about 0 volt. The difference in voltages provides an electrostatic force for the attachment of the workpiece to the stencil. An attractive pressure between the stencil and the workpiece ranges from about 0.5 gm-force/cm$^2$ to about 50 gm-force/cm$^2$ and is preferably about 5 gm-force/cm$^2$.

The attachment between the stencil and the workpiece allows for deprotection agents to be introduced onto exposed regions 179 of the workpiece. For example, a deprotection agent 177 such as vapor phase TCA passes over exposed regions of the workpiece, thereby causing selective deprotection of such regions.

Figure 15:
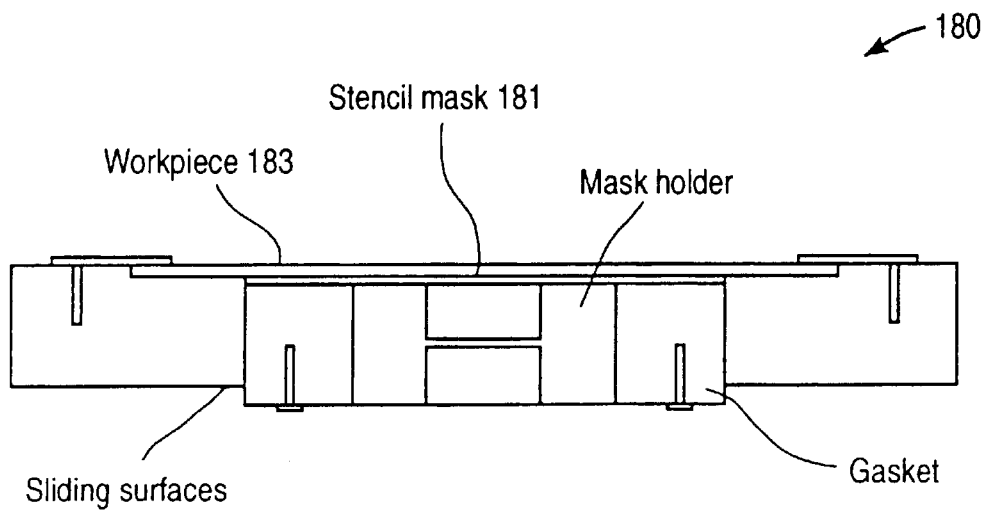
FIG. 15 illustrates a jig used for contacting a mask to a substrate without smearing.

In a preferred embodiment, the apparatus includes a jig 180 for aligning a stencil 181 coated with a loquid barrier material onto the workpiece 183, as illustrated by FIG. 15. The jig substantially prevents the liquid barrier material from smearing onto unselected regions of cells on the workpiece. As shown, the jig includes a workpiece holder 184, a stencil mount 185, sliding surfaces 186, among other features. The stencil mount includes a gasket 187, a stencil holder 188, the stencil mask 181, a spacer 189, sliding surfaces 186, and other features.

To align the coated stencil onto the workpiece, the coated stencil is firmly placed onto the stencil holder of the stencil mount. The stencil mount then inserts into a cavity 191 of the workpiece holder. The coated stencil firmly abuts the surface of the workpiece. The tolerance between the sliding surfaces is about 1.0 micron to about 10.0 microns, and is preferably at about 2.5 microns. An attractive pressure between the stencil and the workpiece ranges from about 0.8 gm-force/cm$^2$ to about 50 gm-force/cm$^2$ and is preferably about 5 gm-force/cm$^2$. A gasket made of a material such as teflon, polyisoprene, polymethyl methacrylate, and others is located between the spacer and the stencil mask mount. This gasket absorbs shock between the stencil and workpiece to seal them together upon an applied pressure.

A further alternative embodiment provides a high resolution stencil mask for ion beam proximity printing, ion beam projection lithography, and the like. The high resolution stencil mask includes, for example, a silicon membrane mask, an epoxy barrier mask, and others. An other example of a high resolution stencil mask may include electroformed nickel, among others. A high resolution stencil mask includes feature sizes of about 0.5 micron to about 50 microns, but less than about 100 microns. A high resolution stencil mask also includes a thickness of about 2 to about 20 microns, and is preferably about 5 microns and less. An example of such mask is made by Nanostructures, Inc.

The high resolution stencil mask attaches to the workpiece by the aforementioned techniques. For example, the stencil mask directly attaches to the surface of the workpiece by placement. Alternatively, the stencil mask may be attached to the workpiece with an interfacial fluid. Further, the stencil mask attaches to the workpiece with use of an electrostatic force, among other forces. The apparatus of FIGS. 14 and 15 may also be used to attach the high resolution stencil onto the workpiece. Of course, the type of high resolution stencil mask depends upon the particular application.

In an alternative embodiment, the present invention provides for the use of vapor phase deprotection agents. The vapor phase deprotection agents may be introduced at low pressure, atmospheric pressure, among others. The use of such vapor phase deprotection agents allows for ease in processing the work piece with linker molecules and barrier material.

Deprotection may be carried out in a directional stream of deprotection agent at low pressure. Low pressure deprotection occurs by first removing the work piece with linker molecules and barrier material from the synthesizer. The work piece is then transferred into a vacuum chamber, preferably an extremely low pressure vacuum chamber. The deprotection agent is then bled into the vacuum chamber at a selected rate to promote directionality of the deprotection agent stream. Preferably, the vacuum chamber includes pressures ranging from about $10^{-5}$ torr to about 1 torr to promote the directionality of the stream. For example, the deprotection agents may include either a 2% solution of TCA in DCP, solid TCA, among others, and combinations thereof. By use of the TCA/DCP solution or solid TCA, the vapor pressure ranges from about 0.1 millitorr to about 1 torr to promote a directional stream of deprotection agents.

In a preferred embodiment, the deprotecting steps occur at atmospheric pressure. At atmospheric pressure, the work piece is held over a solution of deprotection agents at atmospheric pressure, and preferably at room temperature. An example of a deprotection agent includes TCA, DCP, and the like, and combinations thereof. The TCA may be mixed with DCP to form a 2% solution. Alternatively, the TCA may be used in pure form at room temperature, or at a temperature ranging from about 10° C. to about 50° C., and preferably at about 20° C. The work piece is held over the TCA type deprotection agents for about 1 minute or less. The TCA can also be blown against the workpiece by way of forced convection and the like, and even mixed with a water vapor, a carrier gas, or the like.

An advantage of the vapor phase deprotection agent, even at atmospheric pressure, is the lack of mechanical action to disturb any physical barrier pattern material. A further advantage with the vapor phase deprotection agent is the ease in use with selected work pieces.

EXAMPLES

1. Use of Laccuer Barrier Material

An experiment was carried out with a standard 2 inch by 3 inch derivatized glass slide. An ABI Model 392 synthesizer was used to apply PEG linker-CC-DMT (linker layer-2 polymer units-protecting group) on one side of the glass slide. The glass slide, also known as the work piece, was then removed from the reaction chamber of the synthesizer for the application of a barrier material.

To find a suitable barrier material, patterns of candidate materials were applied with a fine paint brush to the linker layer. The fine paint brush produced features made of the barrier material down to about 100 microns. The barrier material was allowed to dry in air, typically at room temperature. The barrier material is intended to provide an enclosure over selected regions of the linker layer. The regions outside the selected regions were exposed for further processing such as a step of deprotection and further synthesis.

In this experiment, a lacquer known as Pactra 63-1 was found to be an effective barrier material. A fine brush applied the lacquer as dots from about 0.1 mm to about 1 mm in dimension to the linker layer. The lacquer was dried for several hours at room temperature, before subsequent processing.

A step of deprotection followed the application of the barrier material. In this experiment, the workpiece was immersed into a deprotecting solution to remove the protecting group from the linker layer.

After deprotecting, the barrier material was stripped. In this experiment, stripping occurred by the use of acetone, gently wiped across the lacquer. The use of acetone in this technique did not affect subsequent coupling processes.

After stripping, the workpiece was reinserted back into the reaction chamber of the synthesizer. In the reaction chamber, the workpiece was fluoreprime coupled. After removing the workpiece from the reaction chamber, a solution of ethylene diamine/ammonia was used to immerse the workpiece for about 5 to 10 minutes.

The workpiece was then placed into a confocal scanning fluorescence microscope for inspection. The deprotected regions fluoresced strongly, and the successfully shielded regions (or selected regions) by the barrier material did not fluoresce. This experiment shows the effectiveness of the lacquer barrier material.

To achieve proper control over the experiment, the experimental and control groups were synthesized and sampled as shown in Table 1.

TABLE 1

Sample and Control Groups for Barrier Material Formation Experiment.

| # | TYPE | PROCESS | RESULT |
|---|------|---------|--------|
| 1 | Control | Apply barrier pattern, strip, and scan. | No fluorescence. |
| 2 | Control | Apply barrier pattern, strip, fluoreprime, and scan. | Complete fluorescence. |
| 3 | Sample | Apply barrier pattern, strip, deprotect, fluoreprime, and scan. | Selective fluorescence. |

Figure 16:
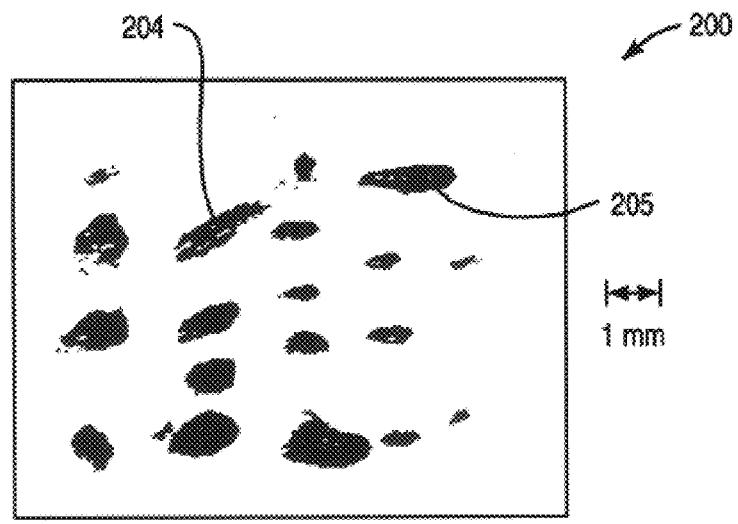
FIG. 16 is a photograph of a fluorescent image of a fluoreprimed workpiece that was selectively shielded from liquid deprotection by a lacquer.

FIG. 16 is a photograph of fluorescent image of the fluoreprimed workpiece that was selectively shielded from liquid deprotection by lacquer. The photograph 200 shows a workpiece 202 with exposed regions 204, and protected regions 205. As noted in Table 1, the layer of barrier material which includes the lacquer effectively shielded the protecting groups, from deprotection. The contrast ratio between the exposed regions and the protected regions 205 is about 20:1.

From this experiment, it is concluded that at least one type of material such as the lacquer can serve as an effective barrier material for complete deprotection and complete protection. The lacquer barrier material is easily applied and dries at room temperature. It is also concluded that at least one type of material such as acetone effectively strips the lacquer from the linker layer but does not affect the coupling process.

2. Use of Vapor-Phase Deprotection

Vapor phase deprotection was carried out on a standard workpiece. The workpiece was a standard 2 inch by 3 inch derivatized glass slide. An ABI Model 392 synthesizer was used to apply PEG linker-CC-DMT (linker layer-2 polymer units-protecting group) on one side of the glass slide. The glass slide also known as the work piece was fluoreprimed, as before. Experiments were performed at a variety of selected barrier materials and deprotection agent pressures as follows.

A. Low Pressure Deprotection

To prove the principles of low pressure deprotection, an experiment was carried out were a deprotection agent is introduced onto the fluoreprimed workpiece at a vacuum. In this experiment, the workpiece was removed from the synthesizer, and inserted into a vacuum chamber. The deprotection agent was bled in through a leak valve at a selected pressure, as measured by vacuum gauges. The vacuum gauges read pressures ranging from about 0.1 millitorr to about 1 torr. At these pressures, the deprotection agent stream should be substantially directional. Two forms of deprotection agents were used in this experiment as follows.

TABLE 2

Low Pressure Deprotection Experiments

| # | PROCESS | RESULT |
|---|---------|--------|
| 1 | Apply 2% solution of TCA in DCP at pressures from about 0.1 millitorr to about 1 torr. | Deprotection partially completed. |
| 2 | Apply TCA from vapor of solid TCA at pressures from about 0.1 millitorr to about 1 torr. | Deprotection partially completed. |

From Table 2, it is clear that applying the deprotection agents at low pressures provided for at least partial deprotection from the deprotection agents. An advantage with the use of the deprotection agents at low pressures is the directionality of the stream of deprotection agents. By controlling the directionality of the deprotection agents, mechanical masks such as stencil masks may be used as a barrier for subsequent processing without being in (intimate) contact with the workpiece.

B. Atmospheric Pressure Gas-Phase Deprotection

An experiment was also performed where the deprotection agents were introduced onto the workpiece at atmospheric pressure. The workpieces were prepared as in the previous experiment at low pressure. A lacquer known as Pactra 63-1 was applied as dots from about 0.1 mm to about 1 mm in dimension to the linker molecule layer of each of the workpieces. The lacquer was dried for several hours at room temperature, before additional processing. The workpieces were then subjected to different deprotecting steps as shown in Table 3.

TABLE 3

Atmospheric Pressure Deprotection Experiments

| # | PROCESS | RESULT |
|---|---------|--------|
| 1 | Hold workpiece over a test tube containing a solution of about 2% TCA/DCP for about 60 seconds. | Complete protection under the lacquer dots and partial deprotection elsewhere. |
| 2 | Hold workpiece over a vial containing solid TCA at about 20° C. for about 60 seconds. | Complete protection under the lacquer dots and complete deprotection elsewhere. |

TABLE 3-continued

Atmospheric Pressure Deprotection Experiments

| # | PROCESS | RESULT |
|---|---------|--------|
| 3 | Hold workpiece over a vial containing solid TCA heated to about 70° C. for about 60 seconds. | Partial protection under the lacquer dots and complete deprotection elsewhere. The lacquer dots did not hold up to the hot TCA, which appeared to condense on the workpiece. |

Each of the samples 1, 2, and 3 was fluoreprimed after deprotection, and scanned to determine the effectiveness of the deprotection agents. From the samples as noted in Table 3, the process of sample 2 has results that appear to be the most effective. Deprotection at room temperature (about 20° C.) with use of solid TCA provided complete protection under the lacquer dots, and complete deprotection elsewhere, clearly desirable results.

C. Atmospheric Pressure Deprotection With Liquid Barrier Materials

Atmospheric deprotection was also carried out using a variety of different barrier materials. These barrier materials include an epoxy such as West 105 (an uncured epoxy resin), a rotary pump oil such as Mowioc MC 110, a silicone oil such as Dow Corning 704, and a polyester such as TAP SB. The workpieces were made as before and the experiments were carried out with the solid TCA deprotection agent at room temperature. Samples were held over the solid TCA for a period of about 20 to about 60 seconds. All of the liquids appeared to act as effective barriers, that is, protection occurred underlying the liquid regions. The West 105 epoxy appeared to give the best results by having the crispest edges, and was therefore chosen for later experiments as described herein.

Figure 17:
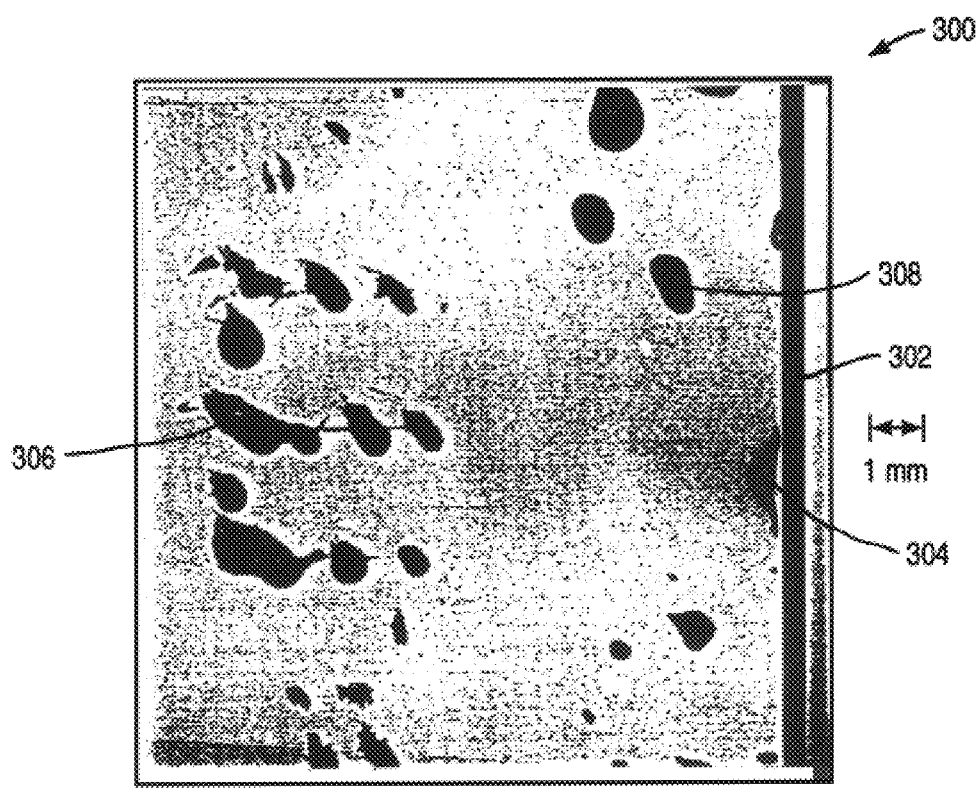
FIG. 17 is a photograph, of dots of uncured epoxy and pump oil overlying a workpiece.

FIG. 17 is a photograph of dots of uncured epoxy and pump oil overlying a workpiece. The photograph 300 shows a workpiece 302 with exposed regions 304, and protected regions 306, 308. As shown, the protected regions include painted-on patches of uncured epoxy 306 (the patches on the left-side of the dotted line), and patches of vacuum pump oil 308 (the patches on the right-side of the dotted line). From the photograph, the patches of uncured epoxy appeared to have crisper edges than the patches of vacuum pump oil. The contrast ratio for the uncured epoxy was about 20:1.

D. Atmospheric Pressure Deprotection with Local Selectivity

Experiments were performed with use of the apparatus of FIG. 14 and a liquid interface between a workpiece and a stencil mask. The stencil mask was electroformed nickel, and coated uniformly with a layer of liquid barrier material such as an epoxy or a polyester. In this experiment, the liquid was prepared by dissolving the West 105 epoxy material in acetone. A solution of 0.1 ml. epoxy in 10 ml. acetone was applied to glass slide via a Sonotek ultrasonic spray nozzle. The glass slide was then spun at about 3000 revolutions per minute such that the surface with solution is normal to the axis of revolution. Of course, the rotation speed and duration depends upon the desired film thickness of remaining solution. The glass slide was then placed film side down onto the stencil mask. An electrode at about 22 kv on a back surface of the glass slide applies electrostatic force onto the workpiece, typically at about an attractive pressure of about 200 Pa (or about $2 \times 10^{-3}$ atmospheres or 2 grams-force/$cm^2$). The glass slide is then removed from the mask which retains a coating of barrier material.

Alignment of the coated stencil mask with workpiece occurred with use of the jig apparatus of FIG. 15. The jig apparatus brought the stencil mask in contact with the workpiece without smearing more than a small fraction of a cell size, typically about 2.5 microns in this experiment. A mask using a 1,000 mesh/inch (25 micron pitch) grid was used as a stencil mask.

Figure 18:
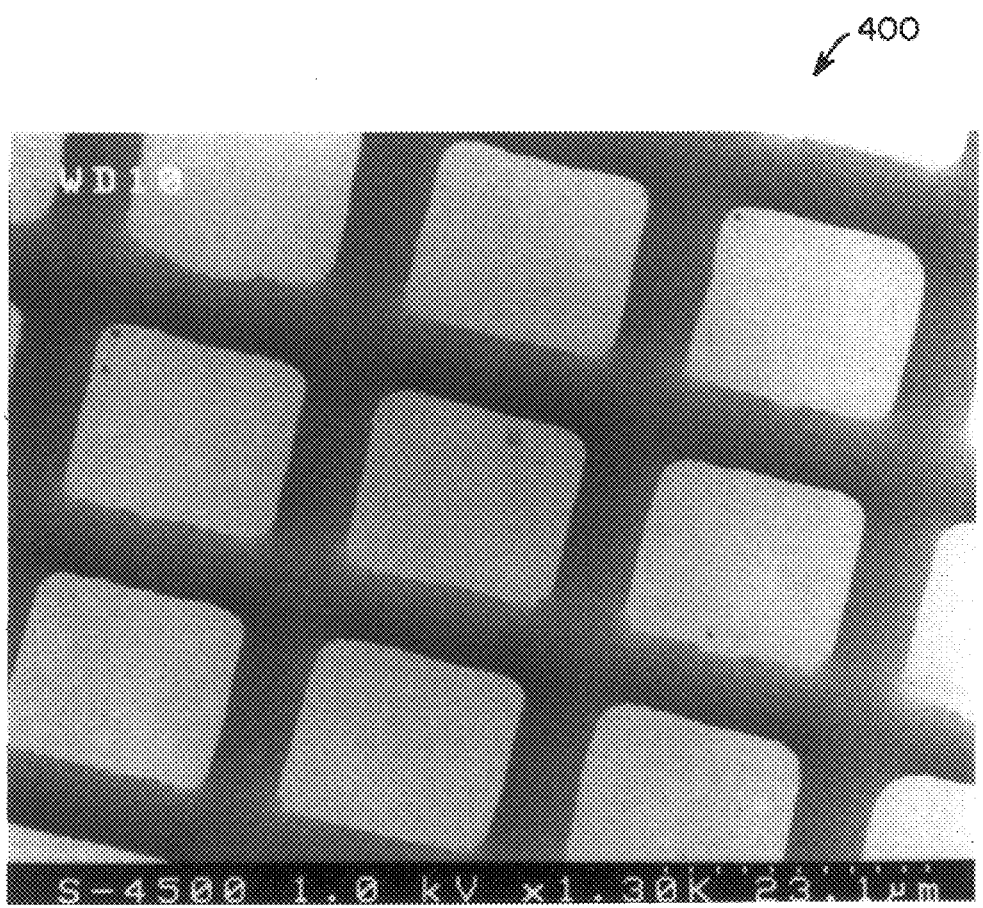
FIG. 18 illustrates a SEM photograph of a liquid uncured epoxy pattern on a glass workpiece.

FIG. 18 illustrates a SEM photograph 400 at 1300 times magnification of a liquid uncured epoxy pattern on a glass workpiece (following removal from stencil mask). As shown, the photograph includes a glass workpiece 402, a grid pattern of uncured epoxy 403, and exposed regions 404. The grid pattern bars are about 7 microns across. This photograph demonstrates the accuracy of the aforementioned apparatus for the placement of an epoxy barrier material onto a workpiece surface without smearing.

FIG. 19 illustrates a SEM photograph 500 of a 100 micron resolution sample. The photograph 500 shows a workpiece 502 with exposed regions 504, and protected regions 506. The workpiece was prepared as before. A stencil mask made of nickel was coated with West 105 epoxy (an uncured epoxy resin) and electrostatically held against the workpiece. Each of the spaces between the protected regions was about 100 microns in length from inner edge to inner edge. The contrast ratio between the exposed and protected regions was about 200:1. This photograph clearly shows the effectiveness of present apparatus and West 105 epoxy. It should be noted that the arc shaped region 508 was caused by West 105 epoxy applied with a fine paint brush.

FIG. 20 illustrates a SEM photograph of a 75 micron resolution sample. The workpiece was prepared as before. The photograph 600 shows a workpiece 602 with exposed regions 604, and protected regions 606. The workpiece was prepared as before. A stencil mask made of nickel was coated with West 105 epoxy (an uncured epoxy resin) and electrostatically held against the workpiece. Each of the spaces between the protected regions is about 75 microns in length from inner edge to inner edge. The width of each of the bars is about 25 microns. The contrast ratio between the exposed and protected regions was less than that of FIG. 19. As even narrower width bars were attached to the workpiece, the contrast ratio between the exposed and protected regions decreased. The photograph 600 shows a contrast ratio of about 4:1 to about 2:1.

E. Atmospheric Pressure Deprotection Silicon Membrane Mask

An experiment was performed with high resolution silicon stencil masks being fabricated for ion-beam proximity printing and ion beam projection lithography. A mask available from Nanostructures, Inc. with a membrane thickness of about 2 to 4 microns was used. The mask was mounted in openings of about 3 millimeter on an aluminum frame. The masks structure with frame was electrostatically attached to the workpiece without use of an interfacial fluid (because of risk of rupturing the fragile membrane). The workpiece was made, as previously noted, in the manner described above. A step of vapor phase deprotection occurred on the workpiece with mask structure attached. The workpiece was fluoreprimed and scanned, as the previous experiments. In this experiment, the results were encouraging, as illustrated in the photograph of FIGS. 21 and 22.

Figure 21:
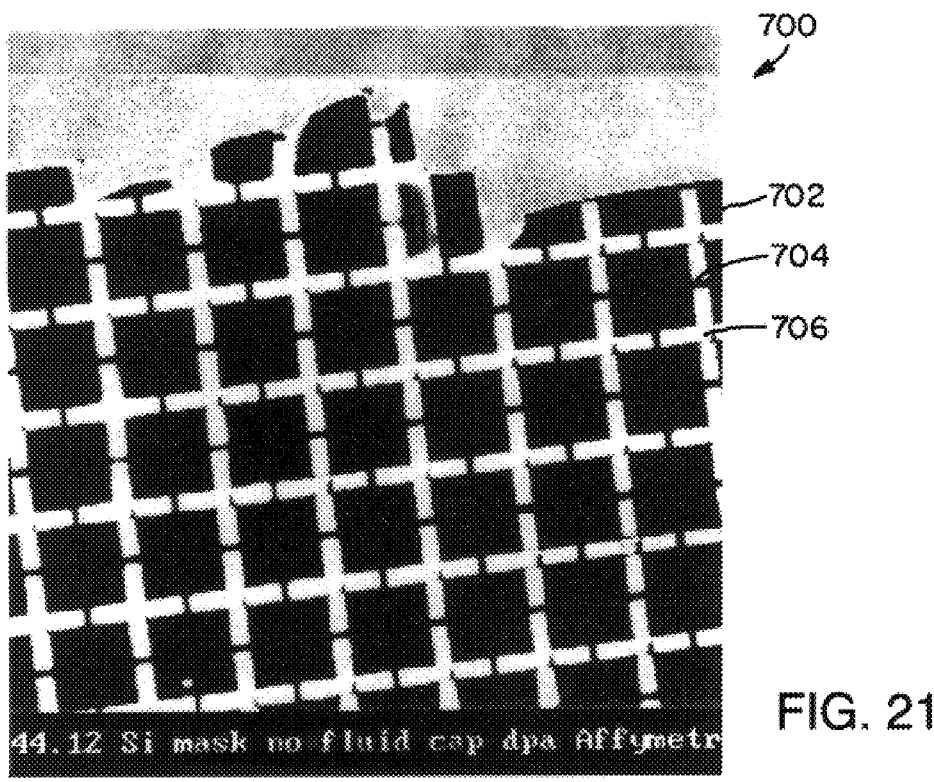
FIG. 21 is a photograph of a fluorescent pattern from vapor deprotection through an uncoated silicon stencil mask.

FIG. 21 is the photograph of fluorescent pattern from the vapor deprotection through the uncoated silicon stencil mask. The photograph 700 includes a workpiece 702 with exposed regions 704 and protected regions 706. As noted, the protected regions were protected by way of the silicon mask. The fluorescent contrast ratios exceeded 10:1 for features of about 50 microns, which are clearly desirable results. No substantial "undercutting" (reaction under the stencil) occurred, presumably due to partial separation caused by particulate contamination.

Figure 22:
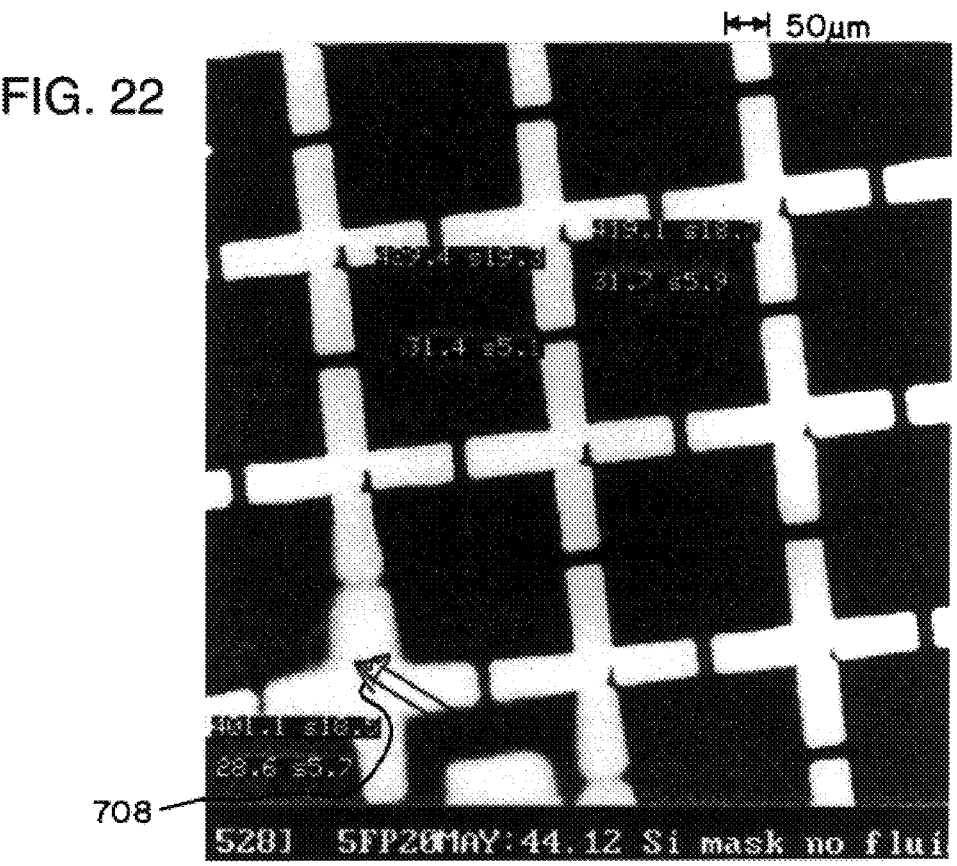
FIG. 22 is a close-up version of the photograph of FIG. 21.

Other regions also suffered from undercutting, as can be seem by the relative sizes of the arrowed features 708 in the FIG. 22 photograph. The undercutting at such regions as defined by the arrow were believed to be caused by particulate contamination preventing good contact. Of course, this problem may be cured, at least in part, by proper process controls, and the like.

In other experiments, less undercutting occurred for smaller features such as about 5 microns and less. It is believed the smaller dimensions due to the smaller features had better contact between workpiece and mask structure. The smaller features are more compliant so the electrostatic force between mask and workpiece surface is more effective at maintaining good contact.

F. Atmospheric Pressure Deprotection with 105 Epoxy Barrier

Experiments were also performed to test the masking strength of 105 epoxy manufactured by West, against vapor phase deprotection. The workpiece samples were prepared, as previously noted, same as the previous experiments up to the deprotecting step. A film of 105 epoxy was spin coated to a thickness of about 0.8+/−0.3 microns (about 1 milligram over about a 4×4 $cm_2$ surface). Thin fragments of silicon were placed at a region near the center of the field of view, and small marks were scored manually nearby, to create an unmasked region. The regions underlying the silicon film were completely masked, the scored regions completely unmasked, and the exposed regions of epoxy film were in question. After placement of such regions, the workpiece was air dried in a desiccator for about 24 hours, before the vapor phase deprotection step.

A vapor phase deprotection step was performed on the sample workpiece described above. The sample was then scanned. The fluorescent count rate for each of the regions are listed in Table 4 below.

TABLE 4

Fluorescent Count Rate for 105 Epoxy Samples

| # | REGION | FLUORESCENT COUNT RATE |
|---|--------|------------------------|
| 1 | Region of exposed 105 epoxy on the workpiece. | about 390 to about 490 |
| 2 | Region of silicon fragments covering the 105 epoxy. | about 330 to about 390 |
| 3 | Region of scored 105 epoxy to form unprotected area. | about 1530 to about 1630 |

The Table 4 illustrates that thin film epoxy blocks at least about 75% of the deprotecting action, for example. Further tests may need to be performed to achieve higher contrasts, between protected and unprotected regions.

Another experiment was performed using a fine grid pattern of 105 epoxy applied to a workpiece. The workpiece was made similar to the technique as described above up to the deprotecting step. A fine, clear, epoxy grid pattern of 25 microns half-pitch was applied to a center region of the workpiece. No epoxy was placed around such center region. Additional widths (down to about 25 microns) of epoxy were applied with an ultra-fine paint brush.

After about 24 hours of air drying in a desiccator, the workpiece under went a step of vapor phase deprotection. A scanned fluorescent image was uniformly bright except for the center region masked by the epoxy pattern. In the masked region, the grid pattern was visible but contrast and brightness were lower. Signal strength in the nominally clear regions of the grid pattern was significantly lower than that from regions more than about 100 microns from the epoxy pattern. Accordingly, it appears as if the West 105 material inhibits the deprotection within regions of about 100 microns of such material.

Other experiments were performed using finer marks of the 105 epoxy, an epoxy paint (TAP "Copon" Clear), a polyester resin (TAP plastics), and a Dow Corning 704 silicone oil. At low magnification the results were as before, that is, the fluorescent image of the oil marks had poor acuity, but the polyester and epoxy matter were fine. However at high magnification (resolution at about 100 microns and less) the 105 wpoxy did have less sharp of an edge than either the epoxy paid or the polyester marks. In particular, the epoxy paint pattern showed the 1 micron pixel size of the scanner, and was therefore determined the preferred barrier material.

G. Atmospheric Pressure Deprotection with TAP "Copon" Clear Paint

In the experiment with use of epoxy paint, printed patterns of the TAP "Copon" clear paint were formed by painting on a solution of 1:4 (paint:spray thinner) on to a 500 mesh/inch nickel grid (Buckbee Mears). The grid with fresh paint was then electrostatically attached to the workpiece, transferring the paint pattern on the surface of the workpiece. The grid was then removed from the surface of the workpiece, leaving the paint pattern behind.

Figure 23:
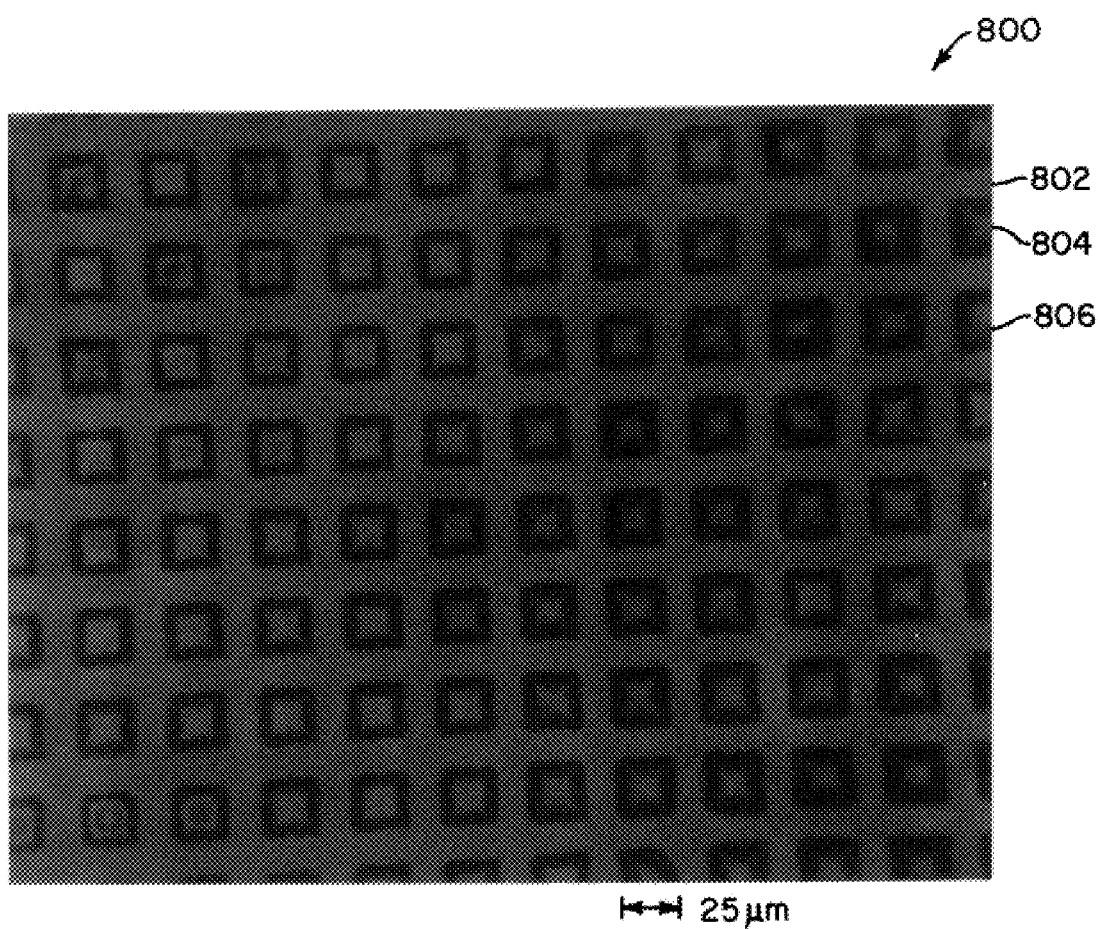
FIG. 23 is a photograph of an epoxy paint pattern transferred from a nickel grid.

FIG. 23 is a photograph 800 of the paint pattern transferred from the nickel grid. The photograph 800 includes a workpiece 802 with an epoxy paint pattern 804 and exposed regions 806. The distance in each of the exposed regions is about 25 microns, and the pattern includes bars, each having a width of about 20 microns. This type of printing is an example of high resolution gravure printing, as described above. The transferred paint pattern acted as the barrier material during subsequent deprotecting steps. As shown, the paint patterns were crisp (and fine lined) to create an effective mask for printing a barrier pattern to obtain a diverse array of oligonucleotides.

Figure 24:
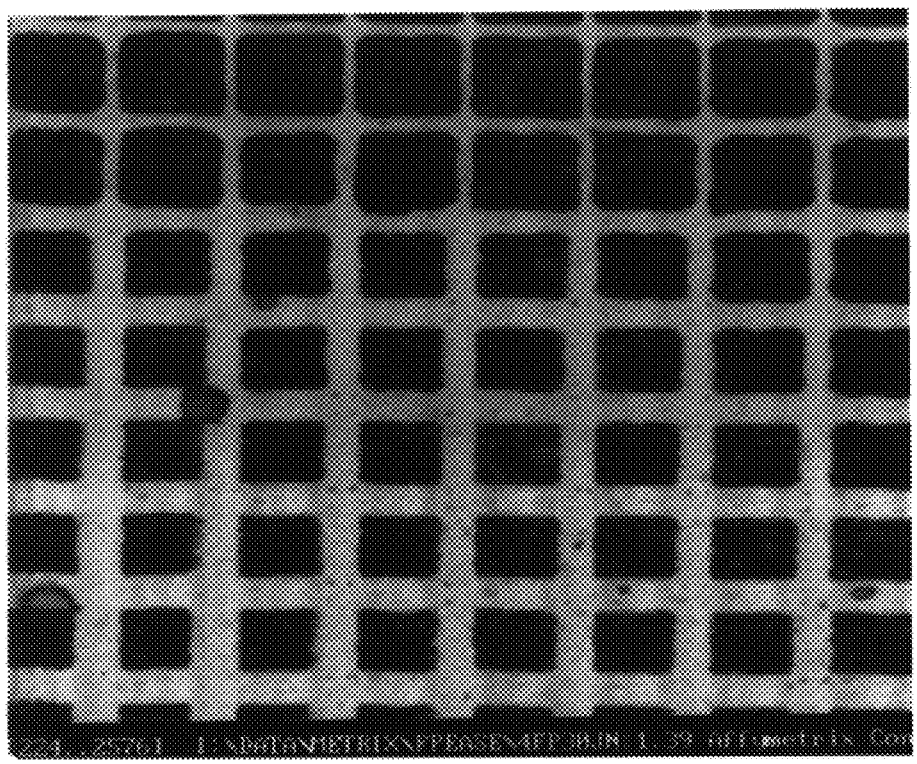
FIGS. 24 and 25 are photographs of fluorescent images resulting from vapor phase deprotection through an epoxy pattern.
Figure 25:
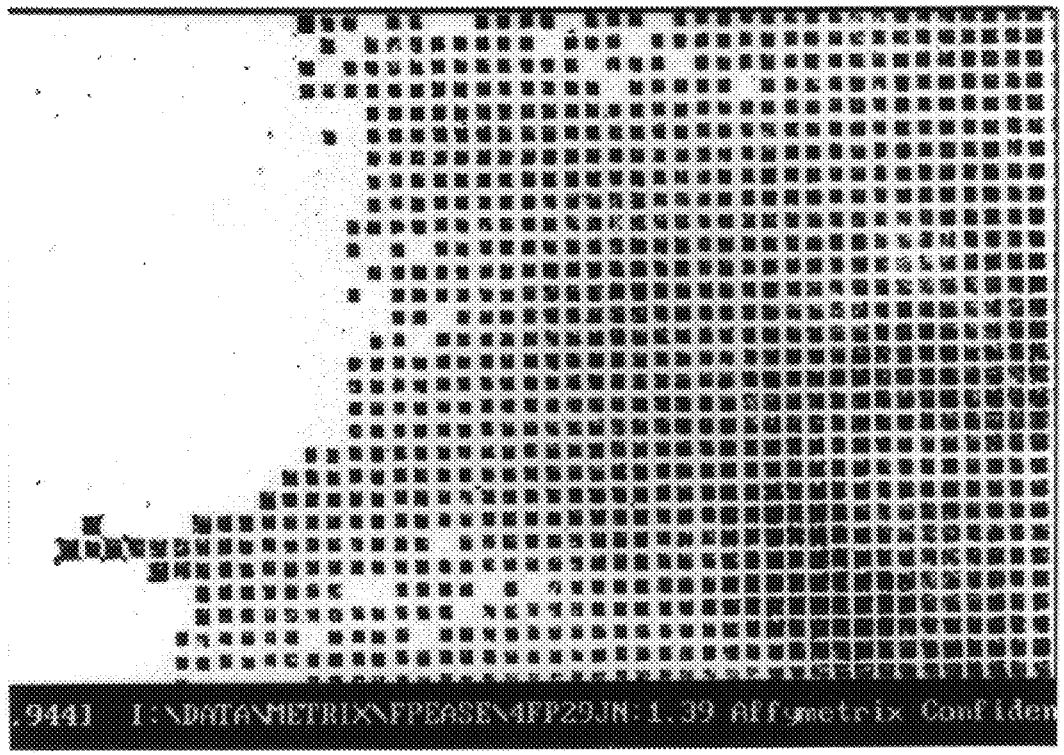

FIGS. 24 and 25 are photographs of fluorescent images resulting from vapor phase deprotection through an epoxy pattern, similar to the one shown by the photograph of FIG. 23. Both of the photograph show good contrast ratios between the exposed and protected regions. The photographs do not show any visible proximity effect and the contrast ratio exceeds 10:1, clearly desirable results.

3. Hybridization Experiments

Figure 26:
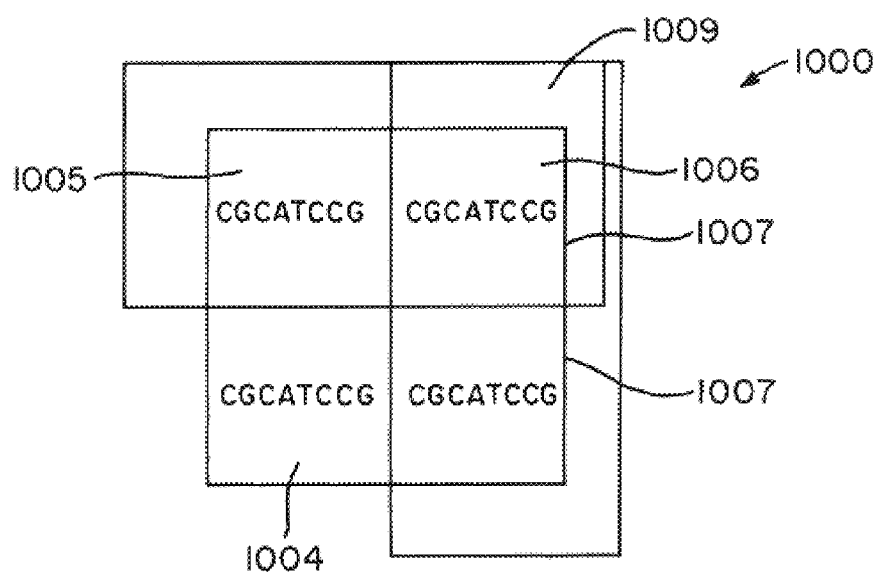
FIG. 26 illustrates a 2×2 array of oligonucleotides formed by masking out deprotection agents after A (vertical mask) and a first T in the synthesis of 3'-CGCATTCCG.

To demonstrate the effectiveness of the aforementioned techniques on the synthesis of oligonucleotides, selected experiments were performed. 2×2 arrays of oligonucleotides were prepared on substrates 1002 using silicon fragments (pieces of silicon material), which were electrostatically attached as crude masks at base #4 (A) and #5 (T). FIG. 26 illustrates a 2×2 array 1000 of oligonucleotides formed by masking out the deprotect agents after A (vertical mask 1009) and the first T in the synthesis of 3'-CGCATTCCG 1004. A 10 nM target 5'-GCGTAGGC-fluorescein at 15 C. was exposed in the flow cell to the array, which was then scanned with a scanner. The four probes were 3'-CGCATCCG (match) 1005, 3'-CGCTCCG (deletion) 1006, 3'-CGCTTCCG (substitution) 1007, and 3'-CGCATTCCG (addition) 1004.

Figure 27:
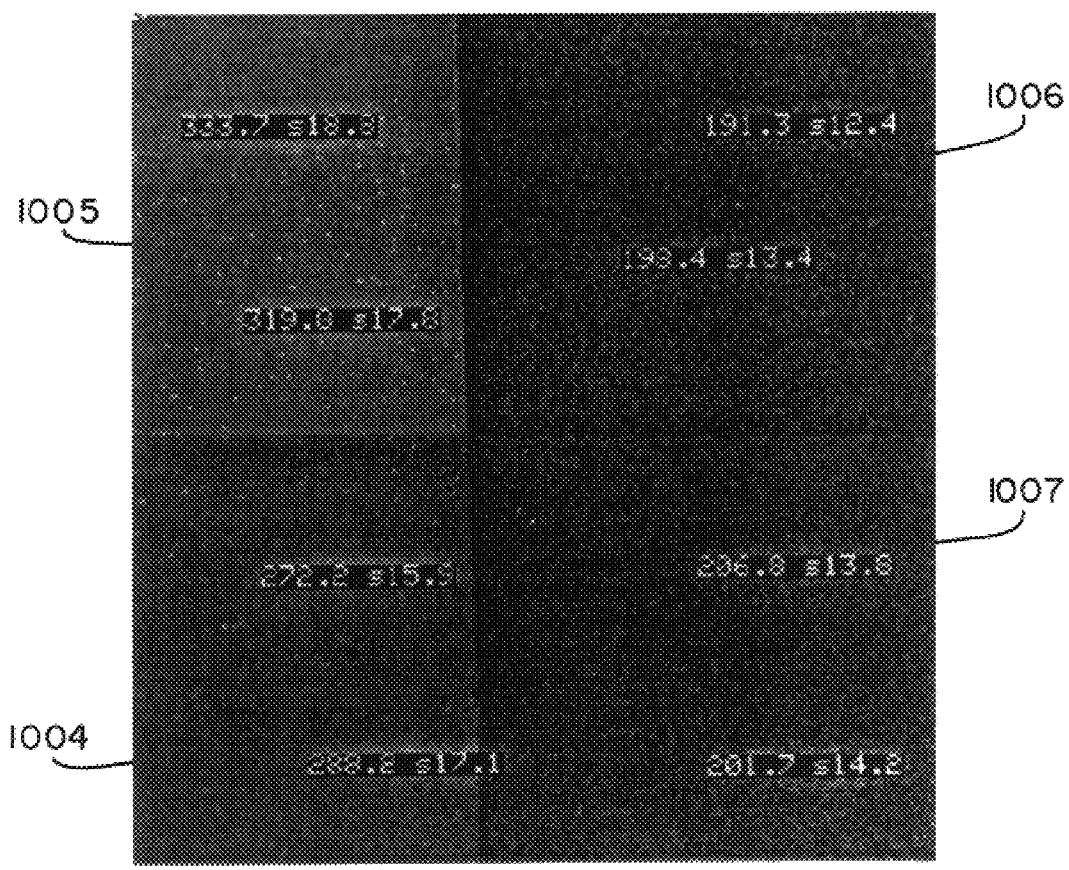
FIG. 27 is a scanned output of an array after hybridizing with 10 nM target oligonucleotide 5'-GCGTAGGC-fluorescein for 15 minutes at 15 C.
Figure 28:
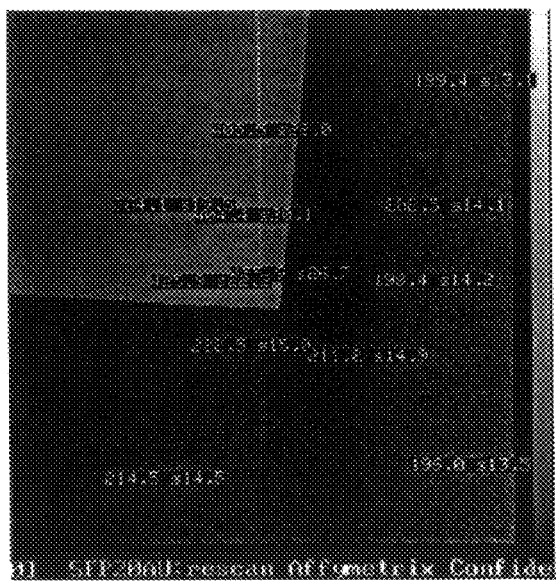
FIGS. 28 and 29 are scanned outputs after hybridizing to a newly-made sample of the same target sequence of FIGS. 26 and 27.
Figure 29:
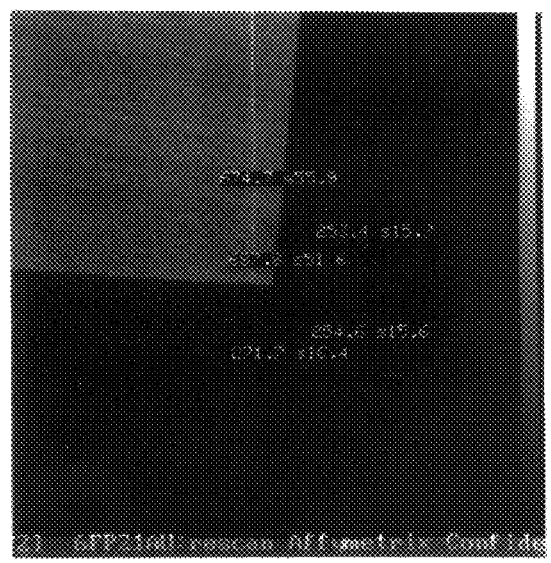
Figure 30:
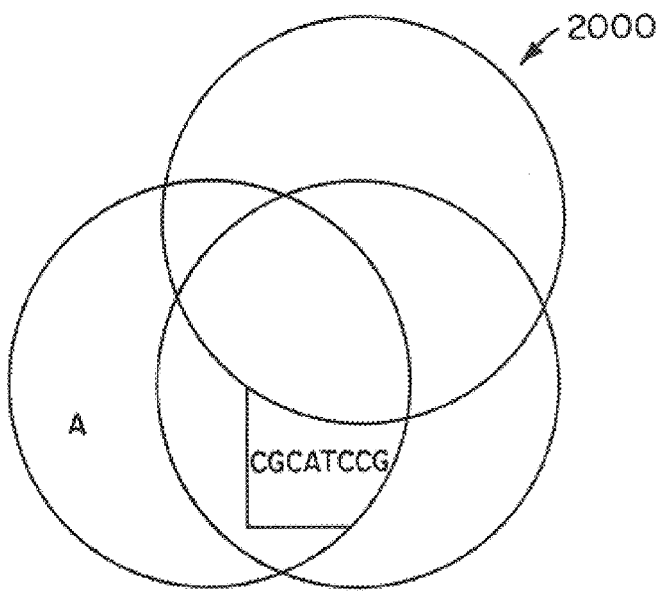
FIG. 30 is an array of same oligos as in FIGS. 26 and 27 made by displacing the reaction chamber when added bases A and the first T in the sequence 3'-CGCATTCCG.

FIG. 27 is a photograph of a representative scanned fluorescent output, which shows the counts obtained in the four areas. The matched area is the most strongly fluorescing, indicating the strongest hybridization to the match and the weakest to the deletion. The white spots appear most frequently in the matching region and was a characteristic of all experiments using this particular target. Another sample was hybridized with a more freshly prepared target oligo and obtained better results (as in FIG. 28) that were further enhanced by hybridizing at 10° C. for 15 minutes and then scanning at 15° C. The counts in the matching region 1005 were more than doubled with only a modest increase in the unmatched regions as shown in FIG. 29.

Because the synthesis of the probes, with the exception of the addition, involved at least one removal from the synthesizer for masked deprotection, control experiments were performed forming the other three probes as uninterrupted sequences on the reverse side of three separate substrates. These sequences were hybridized and scanned to check for any significant difference in counts between those grown uninterruptedly on the reverse side with those grown on the front using the masking. There were no significant differences with those grown on the front using the masking. Hence we conclude that one or two interruptions for masked vapor-phase deprotection introduces no significant undesired perturbation of the growth of the probes.

Figure 31:
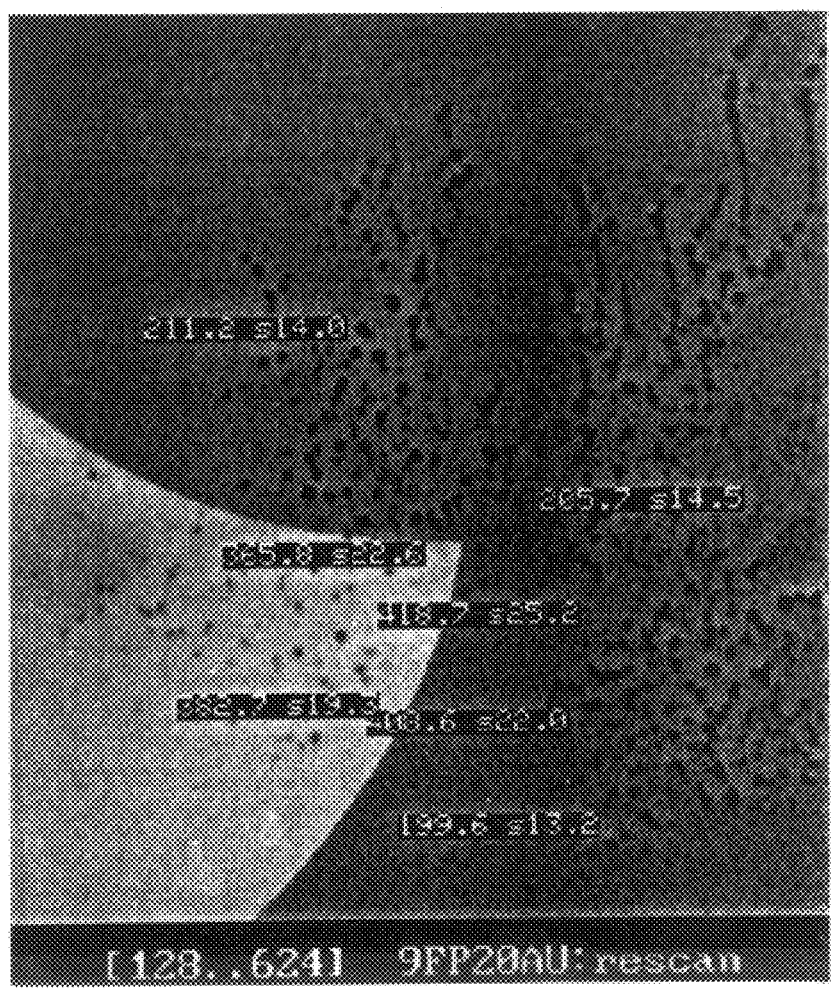
FIGS. 31 and 32 illustrate scanned outputs after hybridizing with 10 nM 5'-GCGTAGGC-fluorescein.
Figure 32:
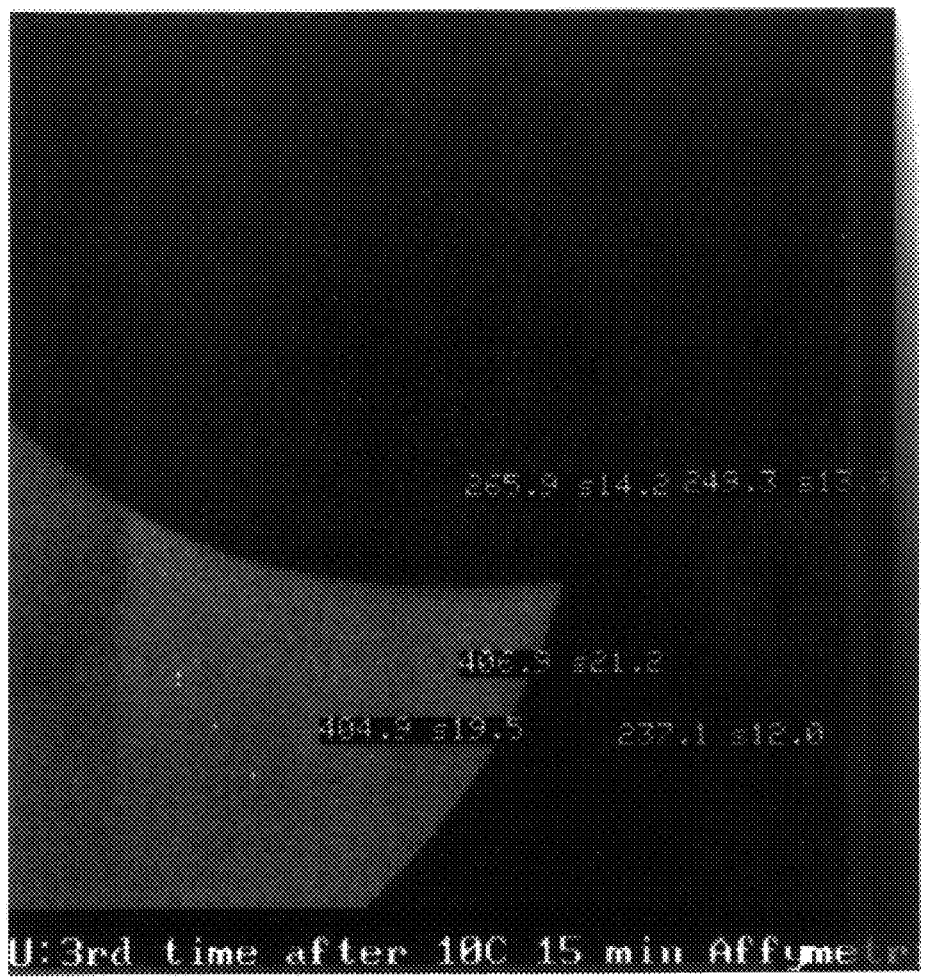

A further check was made on an array 2000 of four oligos of FIG. 26) by moving the reaction chamber around the substrate at bases 4 and 5 as shown by FIG. 31 to compare directly the behavior of a (simple) array made with vapor-phase deprotection at one or two bases with the conventional ABI chemistry throughout. The results are shown in FIGS. 28 and 29. The results were similar to those obtained with the array made with vapor-phase deprotection including the enhanced selectivity and signal from the matching area following hybridization at 10° C. for 15 minutes. Thus no detectable difference between the results obtained with vapor-phase deprotection with those made conventionally were seen.

While the above is a full description of the specific embodiments, various modifications, alternative constructions, and equivalents may be used. For example, while the description above is in terms of the synthesis of oligonucleotide arrays, it would be possible to implement the present invention with peptides, small molecules, other polymers, or the like. Alternatively, the embodiments may also be in context to peptides, other polymers, or the like.

Therefore, the above description and illustrations should not be taken as limiting the scope of the present invention which is defined by the appended claims.

What is claimed is:

1. A method of forming selected polymers on a substrate, said method comprising:

providing a substrate comprising a layer of linker molecules thereon, each of said linker molecules having a protective group at its distal end away from the substrate;

applying a barrier layer overlying said linker molecule layer, said applying step forming selected exposed regions of said linker molecule layer;

exposing said selected exposed regions of said linker molecule layer to a deprotecting agent in a vapor phase, wherein said vapor phase removes more than 80% of the protective groups in said selected exposed regions; and coupling selected monomers to form said selected polymers on the substrate.

2. The method of claim 1, wherein said applying step comprises a printing method selected from the group consisting of: relief press printing, letter press printing, gravure printing, intaglio printing, stencil printing, ion beam proximity printing, ink jet printing, bubble jet printing, lithography, and xerography.

3. The method of claim 1, wherein said applying step comprises a print method selected from the group consisting of stencil printing and lithography.

4. The method of claim 2, wherein said printing method uses a print medium comprising a barrier material, a receptor, a deprotection agent, a monomer, a carrier material, an activator, or a combination thereof.

5. The method of claim 4, wherein said barrier material is selected from the group consisting of: a lacquer, an epoxy, an oil, a polyester, and a polyurethane.

6. The method of claim 4, wherein said barrier material is a liquid.

7. The method of claim 4, wherein the substrate has a top surface and the print medium is selectively applied to said top surface of the substrate.

8. The method of claim 7, wherein said selectively applying step occurs through a drop-on-demand printhead.

9. The method of claim 1, wherein said deprotection agent is an acidic vapor selected from the group consisting of trichloroacetic acid, dichloro acetic acid, hydrochloric acid and any other acidic vapor.

10. The method of claim 1, wherein said deprotection agent comprises water vapor or a carrier gas.

11. The method of claim 1, wherein said deprotection agent is mixed with a carrier gas.

12. The method of claim 1, wherein said deprotection occurs at atmospheric pressure or at a pressure lower than atmospheric pressure.

13. The method of claim 1, wherein said deprotection occurs at a pressure ranging from about 105 torr to about 1 torr.

14. The method of claim 1, wherein said deprotection agent is at a temperature ranging from about 200° C. to about 500° C.

15. The method of claim 1, wherein the polymer is selected from the group consisting of:

nucleic acids, polynucleotides, oligonucleotides, polypeptides, polysaccharides, oligosaccharides, phospholipids, polyurethanes, polyesters, polycarbonates, polyureas, polyamides, polyethyleneimines, polyarylene sulfides, polysiloxanes, polyimides, polyacetates.

16. The method of claim 1, wherein said polymer is selected from the group consisting of: nucleic acids, polynucleotides, oligonucleotides, polypeptides, and polysaccharides.

17. A method of deprotecting selected regions of a substrate, said method comprising: providing a substrate comprising a layer of linker molecules thereon, each of said linker molecules having a protective group;

applying a deprotection agent in vapor phase wherein the vapor phase removes more than 80% of the protective groups on selected regions of said linker molecule layer, wherein said deprotection occurs at atmospheric pressure or at a pressure lower than atmospheric pressure, and wherein said linker molecule layer remains covalently bonded to said substrate after said deprotection.

18. The method of claim 17, wherein said deprotection occurs at a pressure ranging from about 10 torr to about 1 torr.

19. The method of claim 17, wherein said deprotection agent is an acidic vapor selected from the group consisting of trichloroacetic acid, dichloroacetic acid, hydrochloric acid and any other acidic vapor.

20. The method of claim 17, wherein said deprotection agent is at a temperature ranging from about 200° C. to about 500° C.

21. The method of claim 17, wherein said deprotection agent comprises water vapor or a carrier gas.

22. The method of claim 17, wherein said deprotection agent is mixed with a carrier gas.

23. The method of claim 17, wherein said applying step occurs through heat driven forced convection.

24. A method of applying a print medium in a vapor phase in selected regions of a substrate to remove a protective group, said method comprising the steps of:

providing a partially completed substrate comprising an array of monomers, said partially completed substrate having a top surface;

selectively applying a print medium comprising a barrier material, a receptor, a deprotection agent, a monomer group, a carrier material, an activator, or a combination thereof, to selected regions of said substrate top surface;

wherein said vapor phase removes more than 80% of protective groups in the selected regions; and said selectively applying step comprises a printing method selected from the group consisting of: relief press printing, letter press printing, gravure printing, intaglio printing, stencil printing, ion beam proximity printing, ink jet printing, bubble jet printing, lithography, and xerography, and wherein said array of monomers remains covalently bonded to said substrate after applying said print medium.

25. The method of claim 24, wherein said print medium is a deprotection agent selected from the group consisting of trichloroacetic acid, dichioroacetic acid, hydrochloric acid and any other acidic vapor.

26. The method of claim 24, wherein said print medium is a deprotection agent comprising water vapor or a carrier gas.

27. The method of claim 24, wherein said print medium is a deprotection agent is mixed with a carrier gas.

28. The method according to claim 24, wherein said print medium is a deprotection agent and said deprotection occurs at atmospheric pressure or at a pressure lower than atmospheric pressure.

29. The method of claim 24, wherein said print medium is a deprotection agent and said deprotection occurs at a pressure ranging from about 10 torr to about 1 torr.

30. The method of claim 24, wherein said selectively applying step is stencil printing.

31. The method according to claim 24, wherein said lithography is an ion beam projection lithography.

32. The method of claim 24, wherein said monomer is selected from the group consisting of: nucleoside, nucleotide, amino acid, monosaccharide, phospholipid, urethane, ester, carbonate, urea, amide, ethyleneimine, arylene sulfide, siloxane, imide, and acetate.

33. A method of synthesizing nucleic acids or polynucleotides comprising the steps of:

a) providing oligonucleotides having proximal ends and distal ends, said proximal ends coupled to a substrate having a surface, and said distal ends having a removable protective group;

b) removing said protective groups with a deprotection agent in vapor phase to expose functional groups, wherein said vapor phase removes more than 80% of said protective groups, and wherein said oligonucleotides in step a) remain coupled to said substrate after removal of said protective groups; and c) covalently bonding an oligonucleotide to said exposed functional groups.

34. The method of claim 33, wherein the oligonucleotide of step c) has a proximal end and a distal end, the proximal end is bonded to said exposed functional group of step b), and said distal end having a removable protecting group, and wherein the method further comprises repeating the steps b) and c).

35. The method of claim 33, wherein in step a), a plurality of oligonucleotides are coupled to the substrate to form an array.

36. The method of claim 33, wherein said deprotection agent is selected from the group consisting of trichloroacetic acid, dichloroacetic acid, hydrochloric acid and any other acidic vapor.

37. The method of claim 33, wherein said surface of said substrate is selectively protected by a mask during said removing step.

38. The method of claim 37, wherein said mask is selected from a group consisting of an epoxy, a silicone oil, a metal, a silicon material, a lacquer, an oil, a polyester, and a polyurethane.

39. The method of claim 37, wherein said mask is held in place by electrostatic force.

* * * * *